US010835532B2

(12) United States Patent
Messer, Jr. et al.

(10) Patent No.: US 10,835,532 B2
(45) Date of Patent: Nov. 17, 2020

(54) MUSCARINIC AGONISTS AS COGNITIVE ENHANCERS

(71) Applicants: The University of Toledo, Toledo, OH (US); The Board of Trustees of the University of Illinois, Urbana, IL (US)

(72) Inventors: William S. Messer, Jr., Toledo, OH (US); Michael E. Ragozzino, Chicago, IL (US)

(73) Assignees: The University of Toledo, Toledo, OH (US); The Board of Trustees of the University of Illinois, Urbana, IL (US)

(*) Notice: Subject to any disclaimer, the term of this patent is extended or adjusted under 35 U.S.C. 154(b) by 181 days.

(21) Appl. No.: 14/056,616

(22) Filed: Oct. 17, 2013

(65) Prior Publication Data

US 2014/0045863 A1 Feb. 13, 2014

Related U.S. Application Data

(62) Division of application No. 12/992,709, filed as application No. PCT/US2009/043935 on May 14, 2009, now abandoned.

(60) Provisional application No. 61/053,415, filed on May 15, 2008.

(51) Int. Cl.
*A61K 31/506* (2006.01)

(52) U.S. Cl.
CPC .................................. *A61K 31/506* (2013.01)

(58) Field of Classification Search
CPC .......................... A61K 31/506; C07D 276/06
See application file for complete search history.

(56) References Cited

U.S. PATENT DOCUMENTS

| 4,652,641 | A | 3/1987 | Parsons |
| 4,710,508 | A | 12/1987 | Bergmeier et al. |
| 4,786,648 | A | 11/1988 | Bergmeier et al. |
| 5,041,455 | A | 8/1991 | Sauerberg et al. |
| 5,086,053 | A | 2/1992 | Brodin et al. |
| 5,175,166 | A | 12/1992 | Dunbar et al. |
| 5,284,859 | A | 2/1994 | Sauerberg et al. |
| 5,403,845 | A | 4/1995 | Dunbar et al. |
| 5,414,009 | A | 5/1995 | Olesen et al. |
| 5,424,305 | A | 6/1995 | Skalkos et al. |
| 5,512,559 | A | 4/1996 | Skalkos et al. |
| 5,571,826 | A | 11/1996 | Sauerberg et al. |
| 5,618,818 | A | 4/1997 | Ojo et al. |
| 5,712,297 | A | 1/1998 | Sauerberg et al. |
| 5,718,912 | A | 2/1998 | Thompson et al. |
| 5,726,179 | A | 3/1998 | Messer, Jr. et al. |
| 5,744,598 | A | 4/1998 | Skalkos et al. |
| 5,852,037 | A | 12/1998 | Bodick et al. |
| 6,040,442 | A | 3/2000 | Merritt et al. |
| 6,096,767 | A | 8/2000 | Rajeswaran et al. |
| 6,162,791 | A | 12/2000 | Karimian et al. |
| 6,211,204 | B1 | 4/2001 | Messer et al. |
| 6,255,540 | B1 | 7/2001 | Erhardt et al. |
| 6,369,081 | B1 | 4/2002 | Rajeswaran et al. |
| 6,376,675 | B2 | 4/2002 | Messer et al. |
| 6,602,891 | B2 | 8/2003 | Messer et al. |
| 7,265,246 | B2 | 9/2007 | Allen et al. |
| 7,273,857 | B2 | 9/2007 | Kelly et al. |
| 7,291,611 | B2 | 11/2007 | Kelly et al. |
| 7,300,928 | B2 | 11/2007 | Kelly et al. |
| 7,326,731 | B2 | 2/2008 | Allen et al. |
| 7,361,668 | B2 | 4/2008 | Guyaux et al. |
| 2001/0036953 | A1 | 11/2001 | Messer |
| 2003/0032658 | A1 | 2/2003 | Messer et al. |
| 2003/0069290 | A1 | 4/2003 | Wishka et al. |
| 2007/0049576 | A1 | 3/2007 | Barlow et al. |
| 2008/0009520 | A1 | 1/2008 | Kelly et al. |
| 2008/0032965 | A1 | 2/2008 | Hirst et al. |
| 2008/0108618 | A1 | 5/2008 | Brann et al. |
| 2009/0012101 | A1 | 1/2009 | Messer, Jr. et al. |

FOREIGN PATENT DOCUMENTS

| CA | 2113424 | 3/1993 |
| CA | 2434839 | 8/2002 |
| DE | 2242186 | 4/1973 |
| EP | 0060244 B1 | 9/1982 |
| EP | 0239309 B1 | 9/1987 |
| EP | 0244018 B1 | 11/1987 |
| EP | 0259621 A2 | 3/1988 |
| EP | 0296721 A2 | 12/1988 |
| EP | 0307142 B1 | 3/1989 |
| EP | 0316718 B1 | 5/1989 |
| EP | 0349956 A1 | 1/1990 |
| EP | 0384285 A2 | 8/1990 |
| EP | 0384288 A2 | 8/1990 |
| EP | 0459568 A2 | 12/1991 |

(Continued)

OTHER PUBLICATIONS

Messer et al 'Development of CDD-102 as a Selective M1 Agonist for the Treatment of Alzheimer's Disease' Drug Development Research, vol. 57, p. 200-273, 2002.*
Seeger et al 'M2 Muscarinic Acetylcholine Receptor Knock-out Mice Show Deficit in Behavioral Flexabiliy, Working Memory, and Hippocampal Plasticity' The Journal of Neuroscience, 24(45), 10117-10127, 2004.*
E Muir-Broaddus et al., "Neuropsychological test performance of children with ADHD relative to test norms and parent behavioral ratings," Archives of Clinical Neuropsychology, vol. 17, Issue 7 (Oct. 2002).*
Lee et al., "Attention-Deficit Hyperactivity Disorder Symptoms in a Clinic Sample of Children and Adolescents with Pervasive Developmental Disorders," Journal of Child and Adolescent Pharmacology, vol. 16, No. 6., Jan. 2007.*
Canadian Office Action, Application No. 2,434,839 dated Jan. 19, 2009.
European Examination Report, Application No. 01995477.5 dated Jun. 20, 2006.

(Continued)

*Primary Examiner* — Jared Barsky
(74) *Attorney, Agent, or Firm* — MacMillan, Sobanski & Todd, LLC

(57) ABSTRACT

Methods of treating a mental condition by administering to a subject in need thereof an effective amount of compound CDD-102A, [5-(3-ethyl-1,2,4-oxadiazol-5-yl)-1,4,5,6-tetrahydropyrimidine] are described.

5 Claims, 6 Drawing Sheets

(56) References Cited

FOREIGN PATENT DOCUMENTS

| EP | 0630244 | B1 | 12/1999 | |
|---|---|---|---|---|
| EP | 1355646 | B1 | 10/2003 | |
| JP | 2255679 | | 10/1990 | |
| JP | 05-140135 | A | 6/1993 | |
| JP | 6501682 | | 2/1994 | |
| JP | 3411276 | B2 | 11/1994 | |
| JP | 3519062 | B2 | 2/2002 | |
| JP | 2004/520382 | | 7/2004 | |
| WO | 1992/003430 | A1 | 3/1992 | |
| WO | 1993/003726 | A1 | 3/1993 | |
| WO | 1993/014089 | A1 | 7/1993 | |
| WO | 1994/020495 | A1 | 9/1994 | |
| WO | 1994/020496 | A1 | 9/1994 | |
| WO | 1995/005379 | A1 | 2/1995 | |
| WO | 1996/013167 | A1 | 5/1996 | |
| WO | 1998/046231 | A1 | 10/1998 | |
| WO | 2001/05763 | A2 | 1/2001 | |
| WO | WO 01/05763 | A2 * | 1/2001 | ........... C07D 211/00 |
| WO | 2002/060444 | A1 | 8/2002 | |
| WO | 2007/075297 | A2 | 7/2007 | |
| WO | 2007/128674 | A2 | 11/2007 | |
| WO | 2008/118326 | A1 | 10/2008 | |

OTHER PUBLICATIONS

European Examination Report, Application No. 92919345.6 dated Jun. 5, 1997.
European Examination Report, Application No. 01995477.5 dated Jun. 12, 2007.
European Extended Search Report, Applicationn No. 09747565.1, dated Feb. 9, 2012.
Japanese Notificaiton of Reasons for Rejection, Application No. 2001-175844 dated Jun. 30, 2003.
Japanese Notificaiton of Reasons for Rejection, Application No. 5-504463 dated Dec. 12, 2000.
Japanese Notification of Reasons for Rejection, Application No. 2002-560636 dated Jun. 27, 2008.
Japanese Notification of Reasons for Rejection, Application No. 5-504463 dated Sep. 24, 2002.
Japanese Notification of Reasons for Rejection, Application No. 2002-560636 dated Nov. 18, 2009.
PCT International Preliminary Report on Patentability, Application No. PCT/US1992/006842 filed Aug. 3, 1992, dated Nov. 5, 1993.
PCT International Preliminary Report on Patentability, Application No. PCT/US2009/043935 filed May 14, 2009, dated Nov. 25, 2010.
PCT International Preliminary Report on Patentability, Application No. PCT/US2001/047474 filed Dec. 10, 2001, dated May 2, 2003.
PCT International Preliminary Report on Patentability, Application No. PCT/US2006/046840 filed Dec. 8, 2006, dated Jul. 1, 2008.
PCT International Search Report and the Written Opinion, Application No. PCT/US2006/046840 filed Dec. 8, 2006, dated Nov. 23, 2007.
PCT International Search Report and the Written Opinion, Application No. PCT/US2008/003637 filed Mar. 20, 2008, dated Jun. 20, 2008.
PCT International Search Report and the Written Opinion, Application No. PCT/US2009/043935 filed May 14, 2009, dated Jun. 25, 2009.
PCT International Search Report and the Written Opinion, Application No. PCT/US2009/047124 filed Jun. 11, 2009, dated Dec. 3, 2009.
Abood et al., "Anticholinergic Psychotomimetic Agents", International Review of Neurobiology, 1962, vol. 4, pp. 217-273.
Anagnostaras et al., "Selective Cognitive Dysfunction in Acetylcholine M1 Muscarinic Receptor Mutant Mice", Nature Neuroscience, 2003, vol. 6, No. 1, pp. 51-58.
Baumeister et al., "Historical Development of the Dopamine Hypothesis of Schizophrenia", Journal of the History of the Neurosciences, 2002, vol. 11, No. 3, pp. 265-277.
Beers et al., "Structure and Activity of Acetylcholine", Nature, 1970, vol. 228, pp. 917-922.
Bodick et al., "Effects of Xanomeline, a Selective Muscarinic Receptor Agonist, on Cognitive Function and Behavioral Symptoms in Alzheimer Disease", Archives of Neurology, 1997, vol. 54, pp. 465-473.
Bodick et al., "The Selective Muscarinic Agonist Xanomeline Improves Both the Cognitive Deficits and Behavioral Symptoms of Alzheimer Disease", Alzheimer Disease and Associated Disorders, 1997, vol. 11, Supplement 4, pp. S16-S22.
Bosin et al., "Routes to Functionalized Guandidines. The Synthesis of Guanidino Diesters", Journal of Organic Chemistry, 1973, vol. 38, No. 8, p. 1591.
Brimblecombe et al., "The Synthesis & Pharmacology of Some 1,4,5,6,-Tetrahydropyrimidines", British Journal of Pharmacology, 1969, vol. 37, No. 2, pp. 425-435, Abstract Only.
Cao et al., "Synthesis and Biological Characterization of 1-Methyl-1,2,5,6-tetrahydropyridyl-1,2,5-thiadiazole Derivatives as Muscarinic Agonists for the Treatment of Neurological Disorders", Journal of Medicinal Chemistry, 2003, vol. 46, pp. 4273-4286.
Carlsson et al., "Interactions Between Monoamines, Glutamate, and GABA in Schizophrenia: New Evidence", Annual Review of Pharmacology and Toxicology, 2001, vol. 41, pp. 237-260.
Carlsson, "The Current Status of the Dopamine Hypothesis of Schizophrenia", Neuropsychopharmacology, 1988, vol. 1, No. 3, pp. 179-186.
Christopoulos et al., "Synthesis and Pharmacological Evaluation of Dimeric Muscarinic Acetylcholine Receptor Agonists", The Journal of Pharmacology and Experimental Therapeutics, 2001, vol. 298, No. 3, pp. 1260-1268.
Cummings et al., "The Cholinergic Hypothesis of Neuropsychiatric Symptoms in Alzheimer's Disease", American Journal of Geriatric Psychiatry, 1998, vol. 6, No. 2, pp. S64-S78.
Cummings, "The Role of Cholinergic Agents in the Management of Behavioral Disturbances in Alzheimer's Disease", International Journal of Neurophyschopharmacology, 2000, vol. 3, Supplement 2, pp. S21-S29.
Dean, "M1 Receptor Agonism, A Possible Treatment for Cognitive Deficits in Schizophrenia", Neuropsychopharmacology, 2004, vol. 29, pp. 1583-1584.
Dunbar et al., "Design, Synthesis, and Neurochemical Evaluation of 5-(3-Alkyl-1,2,4-oxadiazol-5-yl)-1,4,5,6-tetrahydropyrimidines as m1 Muscarinic Receptor Agonists", Journal of Medicinal Chemistry, 1993, vol. 36, No. 7, pp. 842-847.
Dunbar et al., "Design, Synthesis and Neurochemical Evaluation of 2-Amino-5-(alkoxycarbonyl)-3,4,5,6-Tetrahydropyridence and 2-Amino-5-(alkoxycarbonyl)-1,4,5,6-tetrahydropyridines as M1 Muscarinic Receptor Agonists", Journal of Medicinal Chemistry, 1994, vol. 37, p. 2774.
Felder et al., "Elucidating the Role of Muscarinic Receptors in Psychosis", Life Sciences, 2001, vol. 68, pp. 2605-2613.
Fenton et al., "Breaking the Log-Jam in Treatment Development for Cognition in Schizophrenia: NIMH Perspective", Psychopharmacology, 2003, vol. 169, pp. 365-366.
Fisher et al., "(±)-cis-2-Methyl-Spiro (1,3-Oxathiolane-5,3')Quinuclidine, an M1 Selective Cholinergic Agonist, Attenuates Cognitive Dysfunctions in an Animal Model of Alzheimer's Disease", The Journal of Pharmacology and Experimental Therapeutics, 1991, vol. 257, No. 1, pp. 392-403.
Fisher et al., "±cis-2-methylspiro (1,3-oxathiolane-5,3')-quinuclidine (AF102B): A New M1 Agonist Attenuates Cognitive Dysfunctions in Af64A-Treated Rats", Neuroscience Letters, 1989, vol. 102, pp. 325-331, Abstract Only.
Freedman et al., "A Novel Series of Non-Quaternary Oxadiazoles Acting as Full Agonists at Muscarinic Receptors", British Journal of Pharmacology, 1990, vol. 101, pp. 575-580.
Friedman et al., "Pharmacologic Strategies for Augmenting Cognitive Performance in Schizophrenia", Society of Biological Psychiatry, 1999, vol. 45, pp. 1-16.
Greenhalgh et al., "Acetylation of Some Alkyl-Substituted Guanidines With Acetic Anhydride and Ethyl Acetate", Canadian Journal of Chemistry, 1961, vol. 39, pp. 1017-1029.

(56) References Cited

OTHER PUBLICATIONS

Harries et al., "The Profile of Sabcomeline (SB-202026), A Functionally Selective M1 Receptor Partial Agonist, In the Marmoset", British Journal of Phamacology, 1998, vol. 124, pp. 409-415.
Hatcher et al., "Sabcomeline (SB-202026), A Functionally Selective M1 Receptor Partial Agonist, Reverses Delay-Induced Deficits in the T-Maze", Psychopharmacology, 1998, vol. 138, pp. 275-282.
Hyman et al., "What Are the Right Targets for Psychopharmacology?", Science, 2003, vol. 299, pp. 350-351.
Iadanza et al., "κ-Opioid Receptor Model in a Phospholipid Bilayer: Molecular Dynamics Simulation", Journal of Medicinal Chemistry, 2002, vol. 45, pp. 4838-4846.
Jeppesen et al., "1-(1,2,5-Thiadiazol-4-yl)-4-azatricyclo[2.2.1.02,6]heptanes as New Potent Muscarinic M1 Agonists: Structure-Activity Relationship for 3-Aryl-2-propyn-1-yloxy and 3-Aryl-2-propyn-1-ylthio Derivatives", Journal of Medicinal Chemistry, 1999, vol. 42, pp. 1999-2006.
Jones et al., "Effects of Scopolamine in Comparison with Apomorphine and Phencyclidine on Prepulse Inhibition in Rats", European Journal of Pharmacology, 2000, vol. 391, pp. 105-112.
Jones et al., "Muscarinic Cholinergic Modulation of Prepulse Inhibition of the Acoustic Startle Reflex", The Journal of Pharmacology and Experimental Therapeutics, 2000, vol. 294, No. 3, pp. 1017-1023.
Kelleher et al., "Advances in Atypical Antipsychotics for the Treatment of Schizophrenia", CNS Drugs, 2002, vol. 16, No. 4, pp. 249-261.
Langmead et al., "Muscarinic Acetylcholine Receptors as CNS Drug Targets", Pharmacology & Therapeutics, 2008, vol. 117, pp. 232-243.
Leung-Toung et al., "1,2,4-Thiadiazole: A Novel Cathepsin B. Inhibitor", Bioorganic & Medicinal Chemistry, 2003, vol. 11, No. 24, pp. 5529-5537, Abstract Only.
Levey, "Muscarinic Acetylcholine Receptor Expression in Memory Circuits: Implications for Treatment of Alzheimer's Disease", Proceedings of the National Academy of Sciences (PNAS), 1996, vol. 93, pp. 13456-13541.
Levy et al., "Neuropsychiatric Symptoms and Cholinergic Therapy for Alzheimer's Disease", Gerontology, 1999, vol. 41, Supplement 1, pp. 15-22.
MacLeod et al., "Synthesis and Muscarinic Activities of 1,2,4-Thiadiazoles", Journal of Medicinal Chemistry, 1990, vol. 33, No. 7, pp. 2052-2059.
Messer et al., "Neuroprotective Effects of the M1 Agonist CDD-0102: Promotion of alpha Secretase Activity," Society for Neuroscience Abstract Viewer and Itinerary Planner, vol. 2002 & 32nd Annual Meeting for the Society for Neuroscience, Orlando, Florida, USA, Nov. 2-7, 2002.
Messer, Jr. et al., "Synthesis and Biological Characterization of 1,4,5,6-Tetrahydropyrimidine and 2-Amino-3,4,5,6-Tetrahydropyridine Derivatives as Selective m1 Agonists", Journal of Medicinal Chemistry, 1997, vol. 40, No. 8, pp. 1230-1246.
Messer, Jr. et al., "Synthesis, Biochemical Activity and Behavioral Effects of a Series of 1,4,5,6-Tetrahydropyrimidines as Novel Ligands for M1 Receptors", Bioorganic & Medicinal Chemistry Letters, 1992, vol. 2, No. 8, pp. 781-786.
Messer, Jr., et al., "Tetrahydroprimidine Derivatives Display Functional Selectivity for M1 Muscarinic Receptors in Brain", Drug Development Research, 1997, vol. 40, pp. 171-184.
Messer, Jr., et al., "Design and Development of Selective Muscarinic Agonists for the Treatment of Alzheimer's Disease: Characterization of Tetrahydropyrimidine Derivatives and Development of New Approaches for Improved Affinity and Selectivity for M1 Receptors", Pharmaceutica Acta Helvetiae, 2000, vol. 74, pp. 135-140.
Messer, Jr., et al., "Development of CDD-0102 as a Selective M1 Agonist for the Treatment of Alzheimer's Disease", Drug Development Research, 2002, vol. 57, pp. 200-213.

Moos et al., "Cholinergic Agents: Effect of Methyl Substitution in a Series of Arecoline Derivatives on Binding to Muscarinic Acetylcholine Receptors", Journal of Pharmaceutical Sciences, 1992, vol. 81, No. 10, pp. 1015-1019.
Olesen et al., "3-(3-Alkylthio-1,2,5-Thiadiazole-4-yl)-1-Azabicycles. Structure-Activity Relationships for Antinociception Mediated by Central Muscarinic Receptors", European Journal of Medicinal Chemistry, 1996, vol. 31, No. 3, pp. 221-230, Abstract Only.
Olesen et al., "Preparation of Heterocyclic Compounds as Muscarinic Agonists", Heterocycles, 1994, vol. 120, p. 1167, Abrstact Only.
Olesen et al., "Synthesis and Structural Determination of Stereoisomers of Muscarinic Ligands of the (3-Propylthio-1,2,5-Thiadiazole-4-yl)-1-Azabicycloalkane Type", Chirality, 1997, vol. 9, No. 8, pp. 739-749, Abstract Only.
Orlek et al., "Comparison of Azabicyclic Esters and Oxadiazoles as Ligands for the Muscarinic Receptor", Journal of Medicinal Chemistry, 1991, vol. 34, No. 9, pp. 2726-2735.
Rajeswaran et al., "Design, Synthesis, and Biological Characterization of Bivalent 1-Methyl-1,2,5,6-tetrahydropyridyl-1,2,5-thiadiazole Derivatives as Selective Muscarinic Agonists", Journal of Medicinal Chemistry, 2001, vol. 44, No. 26, pp. 4563-4576.
Ranney et al., "The Pharmacological Actions of Some Guanidine Esters and Their Relationship to Tetrodotoxin", Archives Internationales de Pharmacodynamie et de Therapie, 1968, vol. 175, No. 1, pp. 193-211.
Rasmussen et al., "The Muscarinic Receptor Agonist BuTAC, a Novel Potential Antipsychotic, Does Not Impair Learning and Memory in Mouse Passive Avoidance", Schizophrenia Research, 2001, vol. 49, pp. 193-201.
Sauerberg et al., "Muscarinic Agonists with Antipsychotic-like Activity: Structure-Activity Relationships of 1,2,5-Thiadiazole Analogues with Functional Dopamine Antagonist Activity", Journal of Medicinal Chemistry, 1998, vol. 41, No. 22, pp. 4378-4384.
Sauerberg et al., "Muscarinic Cholinergic Agonists and Antagonists of the 3-(3-Alkyl-1,2,4-oxadiazol-5-yl)-1,2,5,6-tetrahydropyridine Type, Synthesis & Structure-Activity Relationships", Journal of Medicinal Chemistry, 1991, vol. 34, No. 2, pp. 687-692.
Sauerberg et al., "Novel Functional M1 Selective Muscarinic Agonists. Synthesis and Structure-Activity Relationships of 3-(1,2,5-Thiadiazolyl)-1,2,5,6-tetrahydro-1-methylpyridines", Journal of Medicinal Chemistry, 1992, vol. 35, No. 12, pp. 2274-2283.
Sauerberg et al., "Synthesis and Structure-Activity Relationships of Heterocyclic Analogues of the Functional M1 Selective Mescarinic Agonist Hexyloxy-TZTP", Bioorganic and Medicinal Chemistry Letters, 1992, vol. 2, No. 8, pp. 809-814, Abstract Only.
Saunders et al., "2-Methyl-1, 3-Dioxazaspiro [4.5] Decanes as Novel Muscarinic Cholinergic Agonist", Journal of Medicinal Chemistry, 1988, vol. 31, No. 2, pp. 486-491.
Saunders et al., "Ester Bio-isosteres: Synthesis of Oxadiazolyl-1-azabicyclo[2.2.1] Heptanes as Muscarinic Agonist", Journal of the Chemical Society, Chemical Communications, 1988, pp. 1618-1619.
Saunders et al., "Novel Quinuclidine-Based Ligands for the Muscarinic Cholinergic Receptor", Journal of Medicinal Chemistry, 1990, vol. 33, No. 4, pp. 1128-1138.
Schulman et al., "Recognition of Cholinergic Agonists by the Muscarinic Receptor. 1. Acetylcholine and Other Agonists with the NCCOCC Backbone", Journal of Medicinal Chemistry, 1983, vol. 26, No. 6, pp. 817-823.
Seeger et al., "M2 Muscarinic Acetylcholine Receptor Knock-Out Mice Show Deficits in Behavioral Flexibility, Working Memory, and Hippocampal Plasticity",The Journal of Neuroscience, 2004, vol. 24, No. 45, pp. 10117-10127.
Showell et al., "Synthesis and In Vitro Biological Profile of All Four Isomers of the Potent Muscarinic Agonist 3-(3-Methyl-1,2,4-Oxadiazol-5-yl)-1-Azabicyclo [2.2.1] Heptane", Journal of Medicinal Chemistry, 1992, vol. 35, No. 5, pp. 911-916, Abstract Only.
Showell et al., "Tetrahydropyridyloxadiazoles: Semirigic Muscarinic Ligands", Journal of Medicinal Chemistry, 1991, vol. 34, p. 1086.
Silverman, "The Organic Chemistry of Drug Design and Drug Action", Elsevier Academic Press, Second Edition, 2004, pp. 30-31.

(56) References Cited

OTHER PUBLICATIONS

Spalding et al., "Discovery of an Ectopic Activation Site on the M1 Muscarinic Receptor", Molecular Pharmacology, 2002, vol. 61, No. 6, pp. 1297-1302.

Street et al., "Synthesis and Biological Activity of 1,2,4-Oxadiazole Derivatives: Highly Potent and Efficacious Agonists for Cortical Muscarinic Receptors", Journal of Medicinal Chemistry, 1990, vol. 33, No. 10, pp. 2690-2697.

Tecle et al., "A Rationale for the Design and Synthesis of M1 Selective Muscarinic Agonists", Bioorganic & Medicinal Chemistry Letters, 1992, vol. 2, No. 8, pp. 821-826.

Tejada et al., "Design and Synthesis of Novel Derivatives of the Muscarinic Agonist Tetra (ethylene glycol)(3-methoxy-1,2,5-thiadiazol-4-y) [3-(1-Methyl-1,2,5,6-tetrahydropyrid-3-yl)-1,2,5-thiadiazol-4-yl] Ether (CDD-0304): Effects of Structural Modifications on the Binding and Activity of Muscarinic Receptor Subtypes and Chimeras", Journal of Medicinal Chemistry, 2006, vol. 49, No. 25, pp. 7518-7531.

Tzavara et al., "Dysregulated Hippocampal Acetylcholine Neurotransmission and Impaired Cognition in M2, M4 and M2/M4 Muscarinic Receptor Knockout Mice", Molecular Psychiatry, 2003, vol. 8, pp. 673-679.

Tzavara et al., "M4 Muscarinic Receptors Regulate the Dynamics of Cholinergic and Dopaminergic Neurotransmission: Relevance to the Pathophysiology and Treatment of Related Central Nervous System Pathologies", The FASEB Journal, 2004, vol. 18, No. 12, pp. 1410-1412.

Wamoff et al., "Heterocyclische β-Enaminoester: 171. Synthese und Eigenschaften des 2-Amino-3-Äthoxycarbonyl-1,4,5,6-Tetrahydropyridins", Comminications, Synthesis, 1975, pp. 426-427.

Ward et al., "1,2,5-Thiadiazole Analogues of Aceclidine as Potent M1 Muscarinic Agonists", Journal of Medicinal Chemistry, 1998, vol. 41, No. 3, pp. 379-392.

Weinstock et al., "General Synthetic System for 1,2,5-Thiadiazoles", Journal of Organic Chemistry, 1967, vol. 32, No. 9, pp. 2823-2828, Abstract Only.

Wess et al., "Stimulation of Ganglionic Muscarinic M1 Receptors by a Series of Tertiary Arecaidine & Isoarecaidine Esters in the Pithed Rat", European Journal of Pharmacology, 1987, vol. 134, pp. 61-67.

Zhang, "Multiple Muscarinic Acetylcholine Receptor Subtypes Modulate Striatal Dopamine Release, as Studied with M1-M5 Muscarinic Receptor Knock-Out Mice", The Journal of Neuroscience, 2002, vol. 22, No. 15, pp. 6347-6352.

\* cited by examiner

| | $M_1$ receptors | | $M_2$ receptors | | $M_3$ receptors | | $M_4$ receptors | | $M_5$ receptors | |
|---|---|---|---|---|---|---|---|---|---|---|
| | $pEC_{50}$ | $S_{max}$ (%) | $pEC_{50}$ | $S_{max}$ (%) | $pEC_{50}$ | $S_{max}$ (%) | $pEC_{50}$ | $S_{max}$ (%) | $pEC_{50}$ | $S_{max}$ (%) |
| Carbachol | 4.9 ± 0.03 | 100 ± 12 | 7.9 ± 0.23 | 100 ± 6.6 | 4.7 ± 0.23 | 100 ± 14 | 6.0 ± 0.38 | 100 ± 20 | 5.2 ± 0.27 | 100 ± 12 |
| CDD-0102A | 4.9 ± 0.1 | 46 ± 4.1 | n.c. | n.a. | 5.0 ± 0.2 | 6.6 ± 0.8 | n.c. | n.a. | 5.2 ± 0.27 | 28 ± 4.2 | n.a., no significant activity; n.c., not calculable due to lack of activity.

FIG. 7

MUSCARINIC AGONISTS AS COGNITIVE ENHANCERS

CROSS-REFERENCE TO RELATED APPLICATIONS

The present application is a divisional application of U.S. Ser. No. 12/992,709 filed Jan. 24, 2011, pending, which application claims the benefit of the PCT/US09/043935 filed May 14, 2009, which claims priority to the provisional patent application Ser. No. 61/053,415 filed May 15, 2008.

STATEMENT REGARDING SPONSORED RESEARCH

This invention was made with government support under Grants Nos. MH067430 and NS031173 awarded by the National Institutes of Health. The government has certain rights in the invention.

TECHNICAL FIELD AND INDUSTRIAL APPLICABILITY OF THE INVENTION

This invention is directed to methods for enhancing cognitive functions in subjects in need thereof.

BACKGROUND OF THE INVENTION

There is no admission that the background art disclosed in this section legally constitutes prior art.

Although a number of treatments are available to treat the symptoms of mental disorders, relatively few efforts have focused on developing compounds that can improve cognitive function. While recent advances have been made in the understanding of the cholinergic nervous system and the receptors therein, there is still a need to develop compositions which would have a positive effect on a subject's cognitive functions.

One avenue of research being pursued involves cholinergic receptors which are proteins embedded in the cell membrane that respond to the chemical acetylcholine. Cholinergic receptors are subdivided into the nicotinic and muscarinic receptor families, and muscarinic receptors represent a family of five subtypes. Muscarinic receptors mediate a variety of physiological responses to the neurotransmitter acetylcholine in the central and peripheral nervous systems. In particular, $M_1$ muscarinic receptors play a role in learning and memory function in the brain and regulate gastric acid secretion in the stomach. Consequently, muscarinic receptors are being considered as important targets in the treatment of different mental conditions. While an $M_1$ agonist profile could provide efficacy in a broad range of symptomatic domains including enhancement of cognitive function, the development of selective muscarinic agonists has been hindered by the high degree of homology among the five receptor subtypes.

It is difficult to predict whether a muscarinic agonist will have a beneficial result. For example, anticholinergic drugs, including the glycolate esters, produce psychotomimetic effects in humans. In addition, muscarinic antagonists have been used in schizophrenic subjects to control the Parkinsonism associated with administration of antipsychotics with dopamine antagonist activity; yet at higher doses, muscarinic antagonists exacerbate the symptoms of schizophrenia, producing confusion and hallucinations. In contrast, Alzheimer's disease subjects treated with cholinesterase inhibitors, which elevate levels of acetylcholine, exhibit improvements in neuropsychiatric symptoms such as agitation, hallucinations and psychosis. In addition, the selective $M_1/M_4$ muscarinic agonist xanomeline significantly improved psychiatric symptoms such as hallucinations in phase II clinical trials in Alzheimer's subjects. Unfortunately, xanomeline produced unwanted side effects associated with activation of $M_3$ receptors (including salivation, diarrhea and profuse sweating) that limited subject compliance. The side effects seem to be associated with rapid metabolism of the alkyloxy side chain following oral administration, resulting in a nonselective, yet active compound with limited therapeutic utility. Despite a second phase II clinical trial with a patch formulation, the liabilities of xanomeline still outweigh its benefits.

It has also been found that behavioral studies of muscarinic receptor knockout mice also suggest the utility of $M_1$ and $M_4$ agonists in the treatment of psychosis. For example, $M_4$ receptors modulate locomotor activity produced by the stimulation of $D_1$ dopamine receptors. $M_4$ knockout mice also show enhanced sensitivity to the effects of PCP on the pre-pulse inhibition model of psychosis. Since $M_1$ and $M_2$ receptors play a role in cognitive and memory function, agonists with $M_1$ and $M_2$ activity might be particularly useful in treating memory and cognitive deficits associated with schizophrenia.

One of the co-inventors herein has developed different muscarinic agonists, which are claimed in U.S. Pat. Nos. 5,403,845; 5,175,166; 5,726,179; 6,096,767; 6,211,204 B1; 6,369,081 B1; 6,376,675 B2; and 6,602,891 B2; and in PCT patent applications Nos. WO/2007/075397 claiming priority to U.S. Ser. No. 60/754,529); PCT/US08/003637 (claiming priority to U.S. Ser. No. 60/919,800), which are expressly incorporated herein by reference. Also, muscarinic agonists are claimed in U.S. Pat. No. 5,618,818 which is owned by the same assignee as herein.

Efforts to develop muscarinic agonists for the treatment of neurological disorders have been hampered by the high degree of amino acid homology within the binding pocket of muscarinic receptors. While many compounds have been developed with reported selectivity, relatively few compounds have been identified that selectively activate $M_1$ and/or $M_4$ receptors.

This is a particular concern in developing treatments that will enhance cognitive function, rather than only ameliorate functional deficit or impairment. In one example, behavioral studies addressing cognitive aspects of schizophrenia have focused on working memory function since working memory appears to be a core deficit that leads to impairment of other cognitive domains. This is of concern since schizophrenia can lead to a range of cognitive deficits. A prominent cognitive impairment is the subject's inability to inhibit one strategy and learn a new strategy, a deficit that leads to severe impairments in daily living. Abnormalities in pre-frontal cortex-basal ganglia-thalamic circuitry likely contribute to the deficits in cognitive flexibility observed in schizophrenia. Acetylcholine release in these different brain areas appears critical for facilitating cognitive flexibility and attentional processing. More specifically, findings in rodents indicate that increases in acetylcholine output in the pre-frontal cortex and striatum enhance a shift in strategies and attention. In addition, accumulating evidence suggests that muscarinic cholinergic receptors within specific prefrontal-striatal circuitry play a prominent role in facilitating cognitive flexibility.

An additional consideration is the impact of activating muscarinic cholinergic receptors on the strategies utilized in facilitating cognitive function and cognitive flexibility, which can be assessed by measuring the types of errors made in paradigms assessing behavioral flexibility.

Cognitive function reflects the ability to process information and includes various domains of intellectual function including learning and memory, attention or vigilance, language capabilities, and executive functions. Each of these aspects of cognitive function can be further divided into multiple domains. For example, different types of memory function include episodic memory, working memory, reference memory, etc. In a similar fashion, executive function includes reasoning, problem solving, planning, organization and behavioral flexibility.

Errors in perseveration reflect an inability to initially inhibit a previously relevant strategy. Regressive errors reflect an inability to maintain or reliably execute a new strategy once it is selected. The medial prefrontal cortex has been implicated in behavioral flexibility and the ability to shift from previously relevant strategies, while the dorsomedial striatum likely plays a role in mediating the maintenance and execution of novel strategies. Never-reinforced errors are associated with choices that were never reinforced previously and it is not clear which brain regions are involved.

Importantly, because of the complexity of muscarinic cholinergic receptor subtypes, some specific muscarinic receptor subtypes, but not all may prominently enhance cognitive flexibility. Furthermore, alterations in forebrain cholinergic systems are proposed to contribute to the cognitive deficits associated with neurological disorders including Alzheimer's disease and schizophrenia.

Thus, there is a need for the development of pharmacological agents that target specific muscarinic receptor subtypes that can provide novel enhancements and/or treatments for cognitive functions in subjects in need thereof.

However, to date, there are no pharmacological agents that specifically target muscarinic receptor subtypes, leaving unanswered whether activation of muscarinic receptor subtypes enable cognitive flexibility.

In view of the foregoing, it would be desirable to provide muscarinic agonists that result in the selective activation of muscarinic receptors, particularly so side effects are minimized during treatment of the conditions noted above.

Thus, there is a need for muscarinic agonists with activity at $M_1$ receptors which then would useful in the treatment of Alzheimer's disease and schizophrenia, and other cognitive impairment disorders.

It is another object of the present invention to provide compounds that activate $M_1$ receptors which enhance memory function and the various domains of cognitive flexibility.

It is another object of the present invention to provide pharmaceutical composition comprising compounds of the present invention, as active ingredients.

SUMMARY OF THE INVENTION

In one aspect, there is provided a method of treating a mental condition in a subject in need thereof, comprising: administering to a subject in need thereof an effective amount of 5-(3-ethyl-1,2,4-oxadiazol-5-yl)-1,4,5,6-tetrahydropyrimidine hydrochloride (CDD-102A).

In one non-limiting embodiment, the mental condition is selected from the group consisting of cognitive impairment, poor memory confusion, memory loss, and attentional deficits. Other examples include neurodegenerative diseases, Alzheimer's disease, Parkinson's disease, schizophrenia, age-related cognitive decline, and attention-deficit disorder.

In another aspect, there is provided herein a method of modulating the progression of one or more mental conditions of claim that includes administering an effective amount of compound CDD-102A where the effective amount is sufficient to beneficially affect $M_1$ receptor activity.

In still another aspect, there is provided herein a pharmaceutical composition comprising the compound CDD-102A together with pharmaceutically acceptable carriers or excipients.

In a first broad aspect, there is provided herein a composition for prevention of deterioration of a cognitive function, amelioration of a cognitive function and/or enhancement of a cognitive function, the composition comprising an effective amount of a CDD-0102 [5-(3-ethyl-1,2,4-oxadiazol-5-yl)-1,4,5,6-tetrahydropyrimidine] compound, or a pharmaceutically acceptable salt or hydrate thereof.

In certain embodiments, the cognitive function comprises one or more of: executive functioning (such as, for example, planning and prioritizing), reasoning and problem solving, a memory function, a learning function and behavioral flexibility function. In certain embodiments, the behavioral flexibility function includes one or more of: perseveration errors, regressive errors and never-reinforced errors. Cognitive function reflects the ability to process information and includes various domains of intellectual function including learning and memory, attention or vigilance, language capabilities, and executive functions. Each of these aspects of cognitive function can be further divided into multiple domains. For example, different types of memory function include episodic memory, working memory, reference memory, etc. In a similar fashion, executive function includes reasoning, problem solving, planning, organization and behavioral flexibility.

In certain embodiments, the administration of the compound gives rise to efficacious treatment without substantially producing $M_2$, $M_3$, $M_4$ and/or $M_5$ receptor activity in the subject. In certain embodiments, the administration of the compound gives rise to efficacious treatment without substantially producing $M_2$, $M_3$, $M_4$ and/or $M_5$ subtype receptor activity.

In another broad aspect, there is provided herein a composition for prevention of deterioration of a cognitive function, amelioration of a cognitive function and/or enhancement of a cognitive function, the composition comprising an effective amount of a CDD-0102 [5-(3-ethyl-1,2,4-oxadiazol-5-yl)-1,4,5,6-tetrahydropyrimidine] compound, or a pharmaceutically acceptable salt or hydrate thereof;

wherein the cognitive function includes one or more of: executive functioning, reasoning and problem solving, a memory function, a learning function and behavioral flexibility function; wherein the behavioral flexibility function includes one or more of: perseveration errors, regressive errors and never-reinforced errors; and, wherein the administration of the compound gives rise to efficacious treatment without substantially producing $M_2$, $M_3$, $M_4$ and/or $M_5$ subtype receptor activity.

In another broad aspect, there is provided herein a pharmaceutical composition as described herein, together with pharmaceutically acceptable carriers or excipients.

In certain embodiments, the pharmaceutical composition is formulated to be administered to a subject in need thereof in a dosage ranging from about 0.001 mg/kg to about 10 mg/kg body weight.

In certain embodiments, the pharmaceutical composition is formulated to be administered to a subject in need thereof in a dosage ranging from about 0.01 to about 10 mg/kg of body weight.

In certain embodiments, the pharmaceutical composition is formulated to be administered to a subject in need thereof in a dosage ranging from about 0.01 mg/kg to about 0.1 mg/kg of body weight.

In certain embodiments, the pharmaceutical composition is formulated to be administered to a subject in need thereof in a daily dosage.

In certain embodiments, the pharmaceutical composition is formulated to be administered to a subject in need thereof in a regimen of 1 to 4 times per day.

In another broad aspect, there is provided herein a kit comprising at least one pharmaceutically effective dosage unit of a CDD-0102 [5-(3-ethyl-1,2,4-oxadiazol-5-yl)-1,4,5,6-tetrahydropyrimidine] compound, or a pharmaceutically acceptable salt or hydrate thereof;

for administration according to a continuous schedule having a dosing interval selected from one or more of: once daily dosing and/or multiple daily dosing; and, for administration for one or more of: prevention of deterioration of a cognitive function, amelioration of a cognitive function and/or enhancement of a cognitive function in a subject in need thereof;

wherein the cognitive function includes one or more of: executive functioning, reasoning and problem solving, a memory function, a learning function and behavioral flexibility function;

wherein the behavioral flexibility function includes one or more of: perseveration errors, regressive errors and never-reinforced errors; and, wherein the administration of the compound gives rise to efficacious treatment without substantially producing $M_2$, $M_3$, $M_4$ and/or $M_5$ subtype receptor activity.

In another broad aspect, there is provided herein a dosage unit comprising CDD-0102 [5-(3-ethyl-1,2,4-oxadiazol-5-yl)-1,4,5,6-tetrahydropyrimidine] compound, or a pharmaceutically acceptable salt or hydrate thereof, and at least one pharmaceutically acceptable carrier or excipient;

the dosage unit being efficacious for prevention of deterioration of a cognitive function, amelioration of a cognitive function and/or enhancement of a cognitive function in a subject in need thereof;

wherein the cognitive function includes one or more of: executive functioning, reasoning and problem solving, a memory function, a learning function and behavioral flexibility function;

wherein the behavioral flexibility function includes one or more of: perseveration errors, regressive errors and never-reinforced errors; and, wherein the administration of the compound gives rise to efficacious treatment without substantially producing $M_2$, $M_3$, $M_4$ and/or $M_5$ subtype receptor activity.

In another broad aspect, there is provided herein a dosage unit, wherein the dosage unit is a formulation comprising from about 0.001 mg/kg to about 10 mg/kg body weight CDD-0102 [5-(3-ethyl-1,2,4-oxadiazol-5-yl)-1,4,5,6-tetrahydropyrimidine] compound, or a pharmaceutically acceptable salt or hydrate thereof.

In another broad aspect, there is provided herein a dosage unit, wherein the dosage unit is a formulation comprising about 1.0 to about 10 mg/kg body weight CDD-0102 [5-(3-ethyl-1,2,4-oxadiazol-5-yl)-1,4,5,6-tetrahydropyrimidine] compound, or a pharmaceutically acceptable salt or hydrate thereof.

In another broad aspect, there is provided herein a dosage unit, wherein the dosage unit is a formulation comprising from about 0.1 to about 1.0 mg/kg of body weight CDD-0102 [5-(3-ethyl-1,2,4-oxadiazol-5-yl)-1,4,5,6-tetrahydropyrimidine] compound, or a pharmaceutically acceptable salt or hydrate thereof.

In another broad aspect, there is provided herein a dosage unit, wherein the dosage unit is a formulation comprising about 0.01 to about 0.1 mg/kg body weight CDD-0102 [5-(3-ethyl-1,2,4-oxadiazol-5-yl)-1,4,5,6-tetrahydropyrimidine] compound, or a pharmaceutically acceptable salt or hydrate thereof.

In another broad aspect, there is provided herein a dosage unit, wherein the dosage unit is a formulation comprising from about 0.01 mg/kg to about 0.1 mg/kg of body weight CDD-0102 [5-(3-ethyl-1,2,4-oxadiazol-5-yl)-1,4,5,6-tetrahydropyrimidine] compound, or a pharmaceutically acceptable salt or hydrate thereof.

In another broad aspect, there is provided herein a dosage unit, wherein the dosage unit is a formulation comprising about 0.001 mg/kg to about 0.01 mg/kg of body weight CDD-0102 [5-(3-ethyl-1,2,4-oxadiazol-5-yl)-1,4,5,6-tetrahydropyrimidine] compound, or a pharmaceutically acceptable salt or hydrate thereof.

In another broad aspect, there is provided herein a dosage unit, wherein the dosage unit is a formulation comprising about CDD-0102 [5-(3-ethyl-1,2,4-oxadiazol-5-yl)-1,4,5,6-tetrahydropyrimidine] compound, or a pharmaceutically acceptable salt or hydrate thereof formulated as a daily dosage.

In certain embodiments, the dosage unit is a pharmaceutical formulation.

In certain embodiments, the dosage unit is a solid formulation.

In certain embodiments, the dosage unit is a tablet or capsule formulation.

In certain embodiments, the dosage unit is a tablet formulation.

In certain embodiments, the dosage unit is an oral formulation.

In another broad aspect, there is provided herein a method of treating a subject in need thereof, comprising administering to the subject a therapeutically effective amount of the pharmaceutical composition, thereby treating the subject.

In certain embodiments, the pharmaceutical composition is provided as a plurality of individual dosage forms, and wherein the pharmaceutical composition is provided with a set of instructions directing the administration of at least one of each individual dosage forms so as to improve cognitive function.

In another broad aspect, there is provided herein a method of improving the cognitive function in a subject in need thereof, comprising:

administering to a subject in need thereof an effective amount of CDD-102A [5-(3-ethyl-1,2,4-oxadiazol-5-yl)-1,4,5,6-tetrahydropyrimidine] compound or a pharmaceutically acceptable salt or hydrate thereof, wherein the mental condition comprised one or more of: executive functioning, reasoning and problem solving, a memory function, a learning function and behavioral flexibility function.

In certain embodiments, the method includes wherein the behavioral flexibility function includes one or more of: perseveration errors, regressive errors and never-reinforced errors.

In certain embodiments, the method included administration of the compound which gives rise to efficacious treatment without substantially producing $M_2$, $M_3$, $M_4$ and/or $M_5$ subtype receptor activity in the subject.

In certain embodiments, the mental condition is at least partially due to decreased $M_1$ receptor activity.

In certain embodiments, the subject has a mental condition selected from the group consisting of one or more of: neurodegenerative diseases, Alzheimer's disease, Parkinson's disease, schizophrenia, age-related cognitive decline, and attention-deficit disorder.

In another broad aspect, there is provided herein a method of modulating the progression of one or more mental conditions in a subject in need thereof, comprising administering to the subject an effective amount of CDD-0102 [5-(3-ethyl-1,2,4-oxadiazol-5-yl)-1,4,5,6-tetrahydropyrimidine] compound, or a pharmaceutically acceptable salt or hydrate thereof, to selectively activate $M_1$ receptors in the subject without substantially producing $M_2$, $M_3$, $M_4$ and/or $M_5$ subtype receptor activity in the subject.

In another broad aspect, there is provided herein a method of treating and/or enhancing cognitive function in a subject in need thereof, comprising administering to the subject an effective amount of a CDD-0102 [5-(3-ethyl-1,2,4-oxadiazol-5-yl)-1,4,5,6-tetrahydropyrimidine] compound, or a pharmaceutically acceptable salt or hydrate thereof, to selectively activate $M_1$ receptors in the subject without substantially producing $M_2$, $M_3$, $M_4$ and/or $M_5$ subtype receptor activity in the subject.

In another broad aspect, there is provided herein a method for treating loss of memory in a subject in need thereof, comprising;

administering to the subject an effective amount of a CDD-0102 [5-(3-ethyl-1,2,4-oxadiazol-5-yl)-1,4,5,6-tetrahydropyrimidine] compound, or a pharmaceutically acceptable salt or hydrate thereof, to selectively activate $M_1$ receptors in the subject without substantially producing $M_2$, $M_3$, $M_4$ and/or $M_5$ subtype receptor activity in the subject.

In another broad aspect, there is provided herein a method for treating a subject suffering from memory impairment, comprising;

administering to the subject an effective amount of a CDD-0102 [5-(3-ethyl-1,2,4-oxadiazol-5-yl)-1,4,5,6-tetrahydropyrimidine] compound, or a pharmaceutically acceptable salt or hydrate thereof, to selectively activate $M_1$ receptors in the subject without substantially producing $M_2$, $M_3$, $M_4$ and/or $M_5$ subtype receptor activity in the subject.

In another broad aspect, there is provided herein a method for the treatment or prophylaxis of a disease or condition resulting from dysfunction of $M_1$ receptor transmission in a subject, comprising;

administering to the subject an effective amount of a CDD-0102 [5-(3-ethyl-1,2,4-oxadiazol-5-yl)-1,4,5,6-tetrahydropyrimidine] compound, or a pharmaceutically acceptable salt or hydrate thereof, to selectively activate $M_1$ receptors in the subject without substantially producing $M_2$, $M_3$, $M_4$ and/or $M_5$ subtype receptor activity in the subject.

In certain embodiments, the prophylaxis of the disease includes prevents the development of the disease or condition, and/or whereby the disease or condition has already developed and the subject is protected against worsening of the disease or condition.

In certain embodiments, the disease or condition results from defective or malfunctioning $M_1$ receptors in the subject.

In certain embodiments, the treatment disease or condition results from suppressed $M_1$ receptor transmission in the subject.

In certain embodiments, the subject is a human.

In another broad aspect, there is provided herein a method of selectively activating $M_1$ muscarinic receptor, without substantially activating with $M_2$, $M_3$, $M_4$ and/or $M_5$ receptor activity in a subject, comprising:

contacting $M_1$ receptors in the subject with at least CDD-102A [5-(3-ethyl-1,2,4-oxadiazol-5-yl)-1,4,5,6-tetrahydropyrimidine] compound, or a pharmaceutically acceptable salt or hydrate thereof.

In another broad aspect, there is provided herein a method of ameliorating at least one symptom in a subject of a condition where it is beneficial to increase the level of activity of an $M_1$ muscarinic receptor, comprising:

determining that the subject would benefit from an increased level of activity of at least one of an $M_1$ muscarinic receptor; and, administering an amount of a CDD-102A [5-(3-ethyl-1,2,4-oxadiazol-5-yl)-1,4,5,6-tetrahydropyrimidine] compound, or a pharmaceutically acceptable salt or hydrate thereof, which is therapeutically effective to increase the level of activity of $M_1$ muscarinic receptors in the subject without substantially producing $M_2$, $M_3$, $M_4$ and $M_5$ receptor activity, and to ameliorate the at least one symptom in the subject.

In certain embodiments, the level of activity of $M_2$, $M_3$, $M_4$ and $M_5$ receptor activity is not increased to a level sufficient to cause adverse symptom in the subject.

Various objects and advantages of this invention will become apparent to those skilled in the art from the following detailed description of the preferred embodiment, when read in light of the accompanying drawings.

BRIEF DESCRIPTION OF THE DRAWINGS

FIG. 7 shows Table 1 which summarizes functional data for CDD-0102A with respect to activation of muscarinic receptor subtypes.

DETAILED DESCRIPTION OF THE PREFERRED EMBODIMENTS(S)

Figure 1:
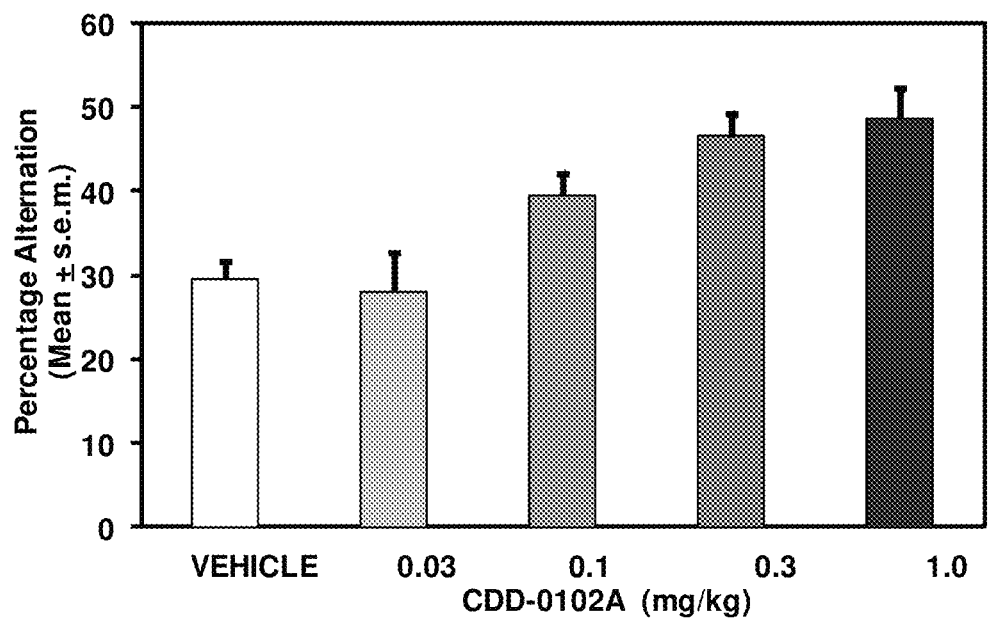
FIG. 1 is a graph showing the effects of i.p. injections of CDD-0102A on delayed spontaneous alternation in a modified T-maze. The number of animals in each group was 8, except for the 0.3 mg/kg dose of CDD-0102A (N=7). *, p<0.05 vs. Controls and CDD-0102A 0.3 mg using Fisher's LSD test.

In one aspect, there is provided methods to the discovery of memory and cognitive enhancing properties of selective $M_1$ muscarinic agonists. It is to be understood that the term "$M_1$" is also referred to as a "muscarinic acetylcholine receptor $M_1$," "cholinergic receptor," and/or "muscarinic 1."

Such compounds can be useful in treating memory and cognitive deficits associated with neurological disorders including schizophrenia.

In another aspect, disclosed herein is a method of increasing the activity of a muscarinic receptor, comprising contacting the receptor with an effective amount of at least one CDD-102A analog compound. CDD-0102 [5-(3-ethyl-1,2,4-oxadiazol-5-yl)-1,4,5,6-tetrahydropyrimidine]. CDD-102 has the Formula I shown below:

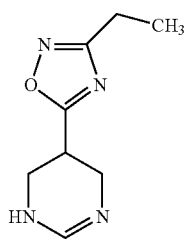

Formula I

CDD102 was synthesized at The University of Toledo and characterized as a selective muscarinic agonist in a variety of binding and functional assays. (Dunbar et al. 1993). The biological data indicate that CDD-0102 is a partial $M_1$ muscarinic agonist with low activity at other muscarinic receptor subtypes. It exhibits a low side effect profile in vivo and reverses memory deficits in rats with impaired cholinergic function. (Messer et al. 2002). See also Dunbar, P. G. et al. (1993). "Design, synthesis, and neurochemical evaluation of 5-(3-alkyl-1,2,4-oxadiazol-5-yl)-1,4,5,6-tetrahydropyrimidines as $M_1$ muscarinic receptor agonists." J Med Chem. 36(7): 842-7; Messer, W. S., Jr. et al. (1997). "Synthesis and biological characterization of 1,4,5,6-tetrahydropyrimidine and 2-amino-3,4,5,6-tetrahydropyridine derivatives as selective m1 agonists." J Med Chem. 40(8): 1230-46; Messer, W. S., Jr. et al. (1997). "Tetrahydropyrimidine derivatives display functional selectivity for $M_1$ muscarinic receptors in brain." Drug Dev. Res. 40: 171-184; and, Messer et al. (2002). "Development of CDD-0102 as a selective $M_1$ agonist for the treatment of Alzheimer's disease." Drug Dev. Res. 57(4): 200-213. In addition, CDD-0102 is generally described in "Muscarinic Agonists," Dunbar, P. G., G. J. Durant, W. Hoss and W. S. Messer, Jr., U.S. Pat. No. 5,403,845, issued Apr. 4, 1995.

In another aspect, disclosed herein is a method of treating a subject suffering from a muscarinic receptor related disorder comprising identifying a subject in need thereof and administering to the subject a therapeutically effective amount of at least one CDD-102A analog compound.

The compounds of Formula I are potentiators of the $M_1$ subtype of muscarinic receptors. Furthermore, the compounds of Formula I selectively potentiate $M_1$ receptors relative to other muscarinic receptors.

By "CDD-102A", "CDD-102A compound" and/or "CDD-102A analog compound," it is generally meant a pharmaceutically acceptable salt or hydrate of the CDD-102 compound.

By "muscarinic related disorder," it is generally meant a disorder whose symptoms are ameliorated by activating a muscarinic receptor.

By "selectively activating $M_1$ receptors," it is generally meant activating $M_1$ receptors in a subject without substantially affecting (e.g., by activating and/or suppressing) other M subtype receptor activity. These other M subtype receptors are generally understood to include $M_2$, $M_3$, $M_4$ and/or $M_5$ receptors. By "selectively activating $M_1$ receptors" in a subject, such subject does not substantially experience symptoms or the effects that are caused by the other M subtype receptors.

In one aspect, there is provided a method of treating a mental condition in a subject in need thereof, comprising: administering to a subject in need thereof an effective amount of 5-(3-ethyl-1,2,4-oxadiazol-5-yl)-1,4,5,6-tetrahydropyrimidine hydrochloride (CDD-102A).

In one non-limiting embodiment, the mental condition is selected from the group consisting of cognitive impairment, poor memory confusion, memory loss, and attentional deficits. Other examples include neurodegenerative diseases, Alzheimer's disease, Parkinson's disease, schizophrenia, age-related cognitive decline, and attention-deficit disorder.

In certain embodiments, the cognitive function comprises one or more of: executive functioning (such as, for example, planning and prioritizing), reasoning and problem solving, a memory function, a learning function and behavioral flexibility function. In certain embodiments, the behavioral flexibility function includes one or more of: perseveration errors, regressive errors and never-reinforced errors.

Cognitive function reflects the ability to process information and includes various domains of intellectual function including learning and memory, attention or vigilance, language capabilities, and executive functions. Each of these aspects of cognitive function can be further divided into multiple domains. For example, different types of memory function include episodic memory, working memory, reference memory, etc. In a similar fashion, executive function includes reasoning, problem solving, planning, organization and behavioral flexibility.

In another aspect, disclosed herein is a method of enhancing cognitive function in a subject, comprising identifying a subject in need thereof and administering to the subject a therapeutically effective amount of at least one CDD-102A analog compound. In some embodiments, the method comprises treating a subject with a pharmacologically active dose of at least one CDD-102A analog compound, for the purpose of controlling the cognitive symptoms associated with loss of cognitive function.

In another aspect, the present invention relates to a method of ameliorating at least one symptom in a subject of a condition where it is beneficial to increase the level of activity of at least one of an $M_1$ muscarinic receptor comprising: determining that the subject would benefit from an increased level of activity of at least one of an $M_1$ muscarinic receptor; and administering an amount of at least one analog of the compound CDD-102A which is therapeutically effective to increase the level of activity of the at least one of an $M_1$ muscarinic receptor and to ameliorate the at least one symptom to the subject.

In another aspect, there is provided herein a method of modulating the progression of one or more mental conditions of claim that includes administering an effective amount of compound CDD-102A where the effective amount is sufficient to beneficially affect $M_1$ receptor activity.

In a first broad aspect, there is provided herein a composition for prevention of deterioration of a cognitive function, amelioration of a cognitive function and/or enhancement of a cognitive function, the composition comprising an effective amount of a CDD-0102 [5-(3-ethyl-1,2,4-oxadiazol-5-yl)-1,4,5,6-tetrahydropyrimidine] compound, or a pharmaceutically acceptable salt or hydrate thereof.

In still other aspects, there is provided herein uses of the CDD-102A compound and/or compositions comprising CDD-102A in improving cognitive function. The cognitive function comprises one or more of: executive function, reasoning and problem solving; a memory function, a learning function and behavioral flexibility function. The behavioral flexibility function includes one or more of: perseveration errors, regressive errors and never-reinforced errors.

In still other aspects, there is provided herein uses of the CDD-102A compound and/or compositions comprising CDD-102A for use in treating a mental condition. In certain embodiments, the mental condition is at least partially due to decreased $M_1$ receptor activity.

In still other aspects, there is provided herein uses of the CDD-102A compound and/or compositions comprising CDD-102A for use in modulating the progression of one or more mental conditions. In certain embodiments, the mental condition is selected from the group consisting of one or more of: neurodegenerative diseases, Alzheimer's disease, Parkinson's disease, schizophrenia, age-related cognitive decline, and attention-deficit disorder.

In still other aspects, there is provided herein uses of the CDD-102A compound and/or compositions comprising CDD-102A for use in treating and/or enhancing cognitive function.

In still other aspects, there is provided herein uses of the CDD-102A compound and/or compositions comprising CDD-102A for use in treating loss of memory.

In still other aspects, there is provided herein uses of the CDD-102A compound and/or compositions comprising CDD-102A for use in treating memory impairment.

In still other aspects, there is provided herein uses of the CDD-102A compound and/or compositions comprising CDD-102A for use in treatment or prophylaxis of a disease or condition resulting from dysfunction of $M_1$ receptor transmission.

In still other aspects, there is provided herein uses of the CDD-102A compound and/or compositions comprising CDD-102A wherein the prophylaxis of the disease includes preventing the development of the disease or condition, and/or whereby the disease or condition has already developed and the subject is protected against worsening of the disease or condition.

In still other aspects, there is provided herein uses of the CDD-102A compound and/or compositions comprising CDD-102A wherein the disease or condition results from defective or malfunctioning $M_1$ receptors in the subject.

In still other aspects, there is provided herein uses of the CDD-102A compound and/or compositions comprising CDD-102A wherein the treatment disease or condition results from suppressed $M_1$ receptor transmission in the subject.

In still other aspects, there is provided herein uses of the CDD-102A compound and/or compositions comprising CDD-102A for use in selectively activating $M_1$ muscarinic receptor, without substantially producing $M_2$, $M_3$, $M_4$ and $M_5$ receptor activity.

In still other aspects, there is provided herein uses of the CDD-102A compound and/or compositions comprising CDD-102A for use in ameliorating at least one symptom in a subject of a condition where it is beneficial to increase the level of activity of an $M_1$ muscarinic receptor.

In still other aspects, there is provided herein uses of the CDD-102A compound or a composition comprising CDD-102A in the manufacture of a medicament for use in improving cognitive function; in the manufacture of a medicament for treating a mental condition; in the manufacture of a medicament for modulating the progression of one or more mental conditions; in the manufacture of a medicament for treating and/or enhancing cognitive function; in the manufacture of a medicament for treating loss of memory; in the manufacture of a medicament for treating memory impairment; in the manufacture of a medicament for the treatment or prophylaxis of a disease or condition resulting from dysfunction of $M_1$ receptor transmission; in the manufacture of a medicament for selectively activating $M_1$ muscarinic receptor, without substantially producing $M_2$, $M_3$, $M_4$ and $M_5$ receptor activity; and. in the manufacture of a medicament for ameliorating at least one symptom in a subject of a condition where it is beneficial to increase the level of activity of an $M_1$ muscarinic receptor.

In still other aspects, there is provided herein a CDD-102A compound or a pharmaceutically acceptable salt or hydrate thereof, or a composition comprising CDD-102A compound or a pharmaceutically acceptable salt or hydrate thereof, for use in treating a mental condition. In certain embodiments, the CDD102A compound selectively activates $M_1$ receptors without substantially producing $M_2$, $M_3$, $M_4$ and/or $M_5$ subtype receptor activity.

In certain embodiments, it is within the scope of the contemplated invention that the CDD-102A analog compounds may be administered in a single daily dose, or the total daily dosage may be administered as a plurality of doses, (e.g., divided doses two, three or four times daily). Furthermore, compounds for the present invention may be administered in intranasal form via topical use of suitable intranasal vehicles, or via transdermal routes, or via topical use of ocular formulations, or using those forms of transdermal skin patches well known to persons skilled in the art.

In one non-limiting example, the selective $M_1$ agonist CDD-0102A enhances learning and memory function in intact animals in three separate memory tasks including spontaneous alternation and two behavioral flexibility paradigms.

Previous work had indicated that muscarinic agonists are effective in enhancing memory function in animals with brain lesions, specifically involving cholinergic pathways that release acetylcholine. One novel and unexpected aspect of the present invention is that muscarinic agonists enhance learning and memory function in normal animals. Moreover, CDD-0102A improves behavioral flexibility by decreasing perseverative errors, regressive errors and never-reinforced errors—an unusual and unexpected combination of behavioral effects that has not been observed with other compounds.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and nonpatent literature, referred to in this specification are expressly incorporated by reference herein.

EXAMPLES

Various neurodegenerative diseases and psychiatric disorders are marked by alterations in brain $M_1$ muscarinic cholinergic receptor function and cognitive deficits including working memory and cognitive flexibility impairments. Alleviating such deficits in conditions such as Alzheimer's disease and schizophrenia has been limited due to a lack of agonists with $M_1$ muscarinic receptor subtype specificity. CDD-102A is a functionally-selective $M_1$ agonist with lower activity at other muscarinic receptor subtypes. The present experiment investigated the effects of systemic treatment with CDD-102A on working memory and/or attentional set-shifting in rats. All testing occurred in a four-arm cross maze. Delayed (30 sec) spontaneous alternation in Long Evans rats was used as a test for working memory. CDD-102A dosed i.p 30 minutes before testing at 0.1, 0.3 and 1 mg/kg significantly enhanced delayed spontaneous alternation performance, suggesting improvement in working memory. However, at all the doses tested, the drug did not alter the number of arm entries suggesting CDD-102A does not have any general effects on locomotor activity. A shift between a place and visual cue discrimination was used as an attentional set-shifting test. In this set of experiments, rats received either vehicle or CDD-102A (0.003-0.1 mg/kg) 30 minutes prior to testing in a place-visual cue set-shifting task.

A treatment was administered either prior to the acquisition phase or prior to the shift phase. Treatment with CDD-102A did not affect acquisition of either a place or visual cue discrimination. In contrast, CDD-102A at 0.03 and 0.1 mg/kg significantly enhanced a shift between a place and visual cue discrimination. Analysis of the errors in the shift to the place or shift to the visual cue strategy revealed that in both cases, CDD-102A significantly increased the ability to initially inhibit a previously relevant strategy and maintain a new, relevant strategy once selected. While not wishing to be bound by theory, the inventors herein now believe that, taken together, the findings show that CDD-102A is useful as a novel treatment in alleviating memory and cognitive flexibility deficits in various neurological disorders and diseases.

Example 1

The effects of CDD-102A (which is a selective $M_1$ muscarinic cholinergic agonist) on spatial working memory were investigated.

To evaluate the effects of muscarinic agonists on memory function in normal animals, rats were tested on a delayed spontaneous alternation task in a modified T-maze. The task takes advantage of rats' natural tendency to alternate. Animals were placed in a 4-arm maze shaped like a "+". If a rat chose four different arms in four consecutive choices it was scored as an alternation. A delay was inserted between arm choices to help assess memory function. In the delay version of the task, CDD-0102A (a functionally selective $M_1$ agonist) improved memory function in a dose dependent manner (see FIG. 1).

Statistical analysis revealed an overall significant effect (p<0.001) and a post-hoc Fisher's LSD test indicated that performance at the 0.1, 0.3 and 1.0 mg dose was significantly different from performances for vehicle controls and the group treated with 0.03 mg of CDD-0102A. In the example shown in FIG. 1, the effects of i.p. injections of CDD-0102A on delayed spontaneous alternation in a modified T-maze are demonstrated. The number of animals in each group was 8, except for the 0.3 mg/kg dose of CDD-0102A (N=7). *, p<0.05 vs. Controls and CDD-0102A 0.3 mg using Fisher's LSD test.

Example 2

Figure 2:
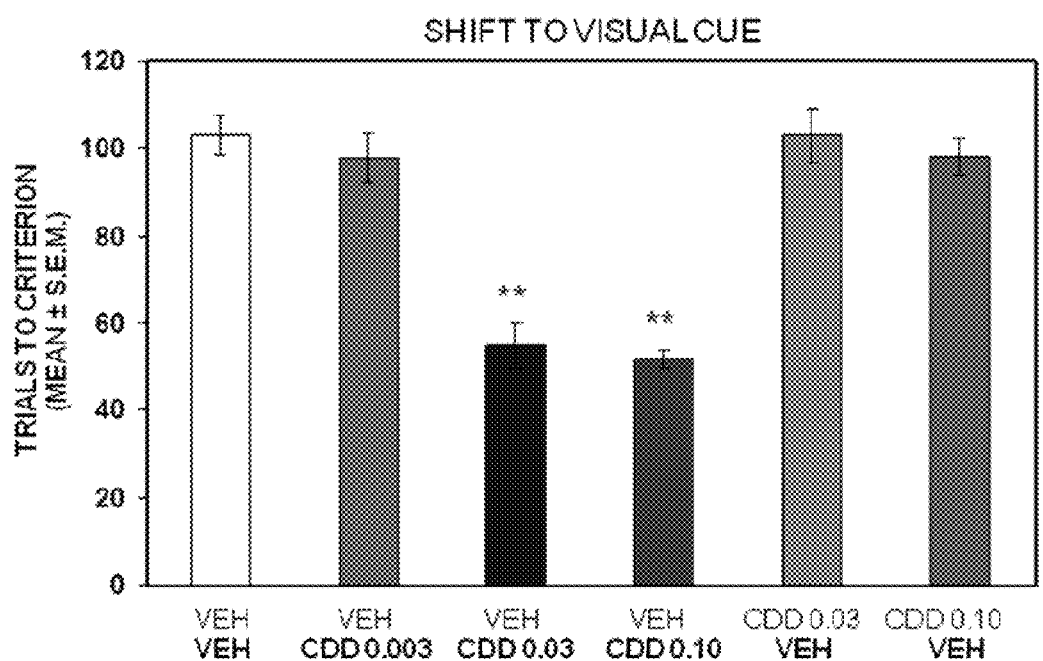
FIG. 2 is a graph showing the results of tests for shifting from a place cue task to a visual cue task. CDD-0102A, at doses of 0.03 and 0.1 mg/kg decreased the number of trials to criterion (10 consecutive correct choices). Vehicle (N=3), CDD-0102A (N=4).

To examine cognitive flexibility, animals were evaluated for their ability to learn a place-visual cue task. Local cues in the maze arms included a black board in one arm and white board in the other arm. The cues were switched between the choice arms randomly across trials so the same cue was not always in the same location. Rats first learned to use a place strategy—always enter the same arm to receive a cereal reinforcement. Criterion was set at 10 consecutive correct trials. No treatment was given to rats prior to learning the place strategy test. The results are shown with the two bars on the left side of the graph in FIG. 2, showing that learning of a place-visual cue task. CDD-0102A, at a dose of 0.03 mg/kg decreased the number of trials to criterion (10 consecutive correct choices). Vehicle (N=3), CDD-0102A (N=4).

The following day, rats had to inhibit using a place strategy and learn a visual cue strategy. That is, a rat had to choose the arm that contained a particular color cue (e.g., black). The criterion again was set at 10 consecutive correct trials. Rats received either saline (N=3) or CDD-0102A at 0.03 or 0.1 mg/kg (N=4) 30 minutes prior to testing. The results are shown in the middle of FIG. 2. Rats treated with CDD-0102A (0.03 or 0.1 mg/kg) required about half the trials to achieve criterion compared to that of controls. Taken together, the data indicate that several behavioral assays are available for assessing cognitive enhancement in rodents.

Figure 3:
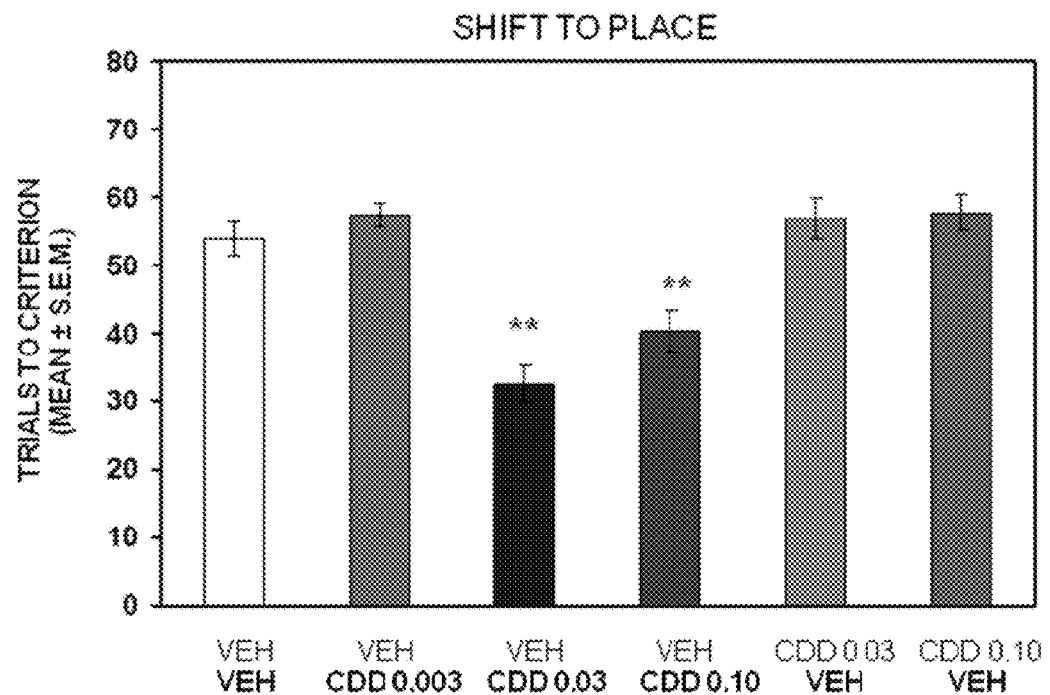
FIG. 3 is a graph showing the results of tests for shifting from a visual cue task to a place cue task. CDD-0102A, at doses of 0.03 and 0.1 mg/kg decreased the number of trials to criterion (10 consecutive correct choices). Vehicle (N=3), CDD-0102A (N=4).

Similar studies evaluated the ability of animals to shift from learning a visual cue task to a place strategy. Again criterion was set at 10 consecutive correct trials. Rats received either saline (N=3) or CDD-0102A at 0.03 or 0.1 mg/kg (N=4) 30 minutes prior to testing. The results are shown in the middle of FIG. 3. Rats treated with CDD-0102A (0.03 or 0.1 mg/kg) required about half the trials to achieve criterion compared to that of controls.

Figure 4A:
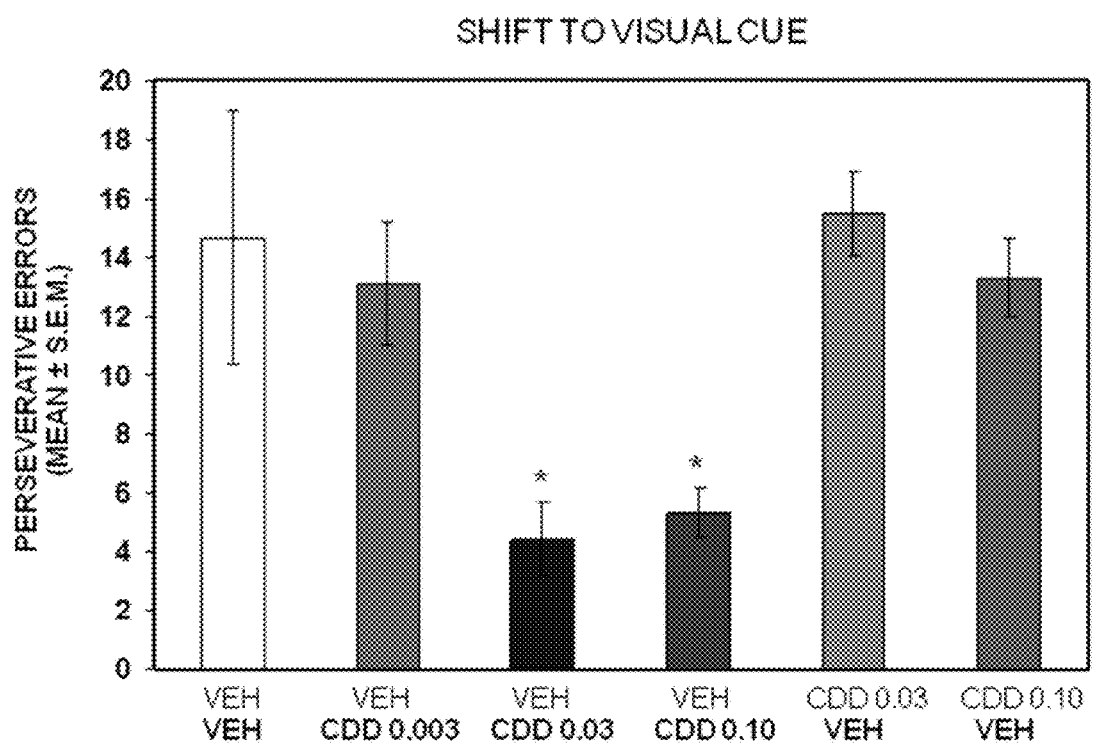
FIGS. 4A-C presents graphs depicting the breakdown of the types of errors exhibited during the shift from a place cue task to a visual cue task. CDD-0102A, at doses of 0.03 and 0.1 mg/kg decreased the number of A) perseverative errors, B) regressive errors and C) never-reinforced errors.
Figure 4B:
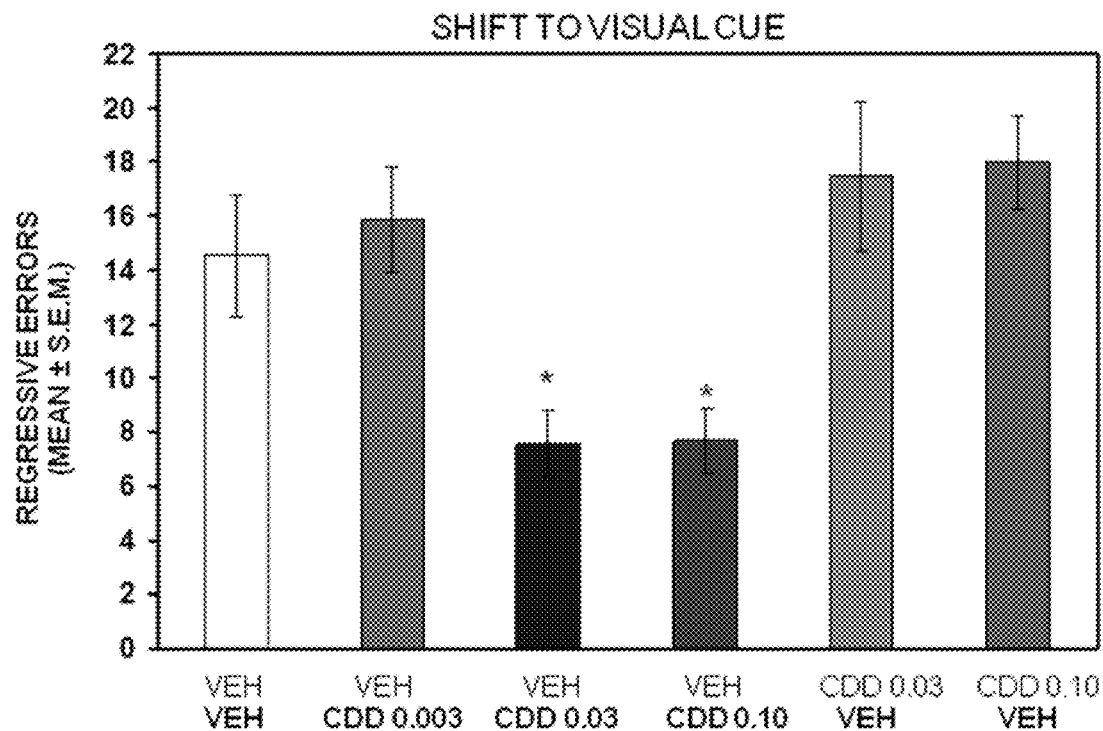
Figure 4C:
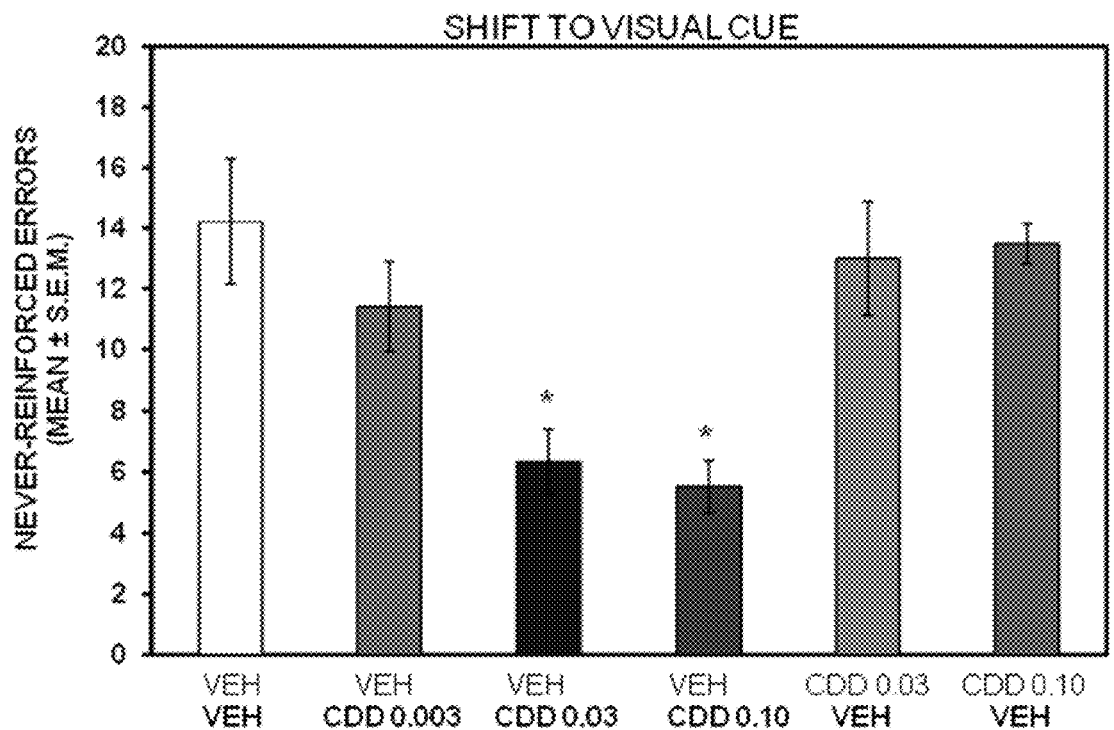

An analysis of the types of errors exhibited during the shift from a place cue task to a visual cue task is shown in FIGS. 4A-C. CDD-0102A, at doses of 0.03 and 0.1 mg/kg decreased the number of: perseverative errors (FIG. 4A) regressive errors (FIG. 4B) and never-reinforced errors (FIG. 4C).

Figure 5A:
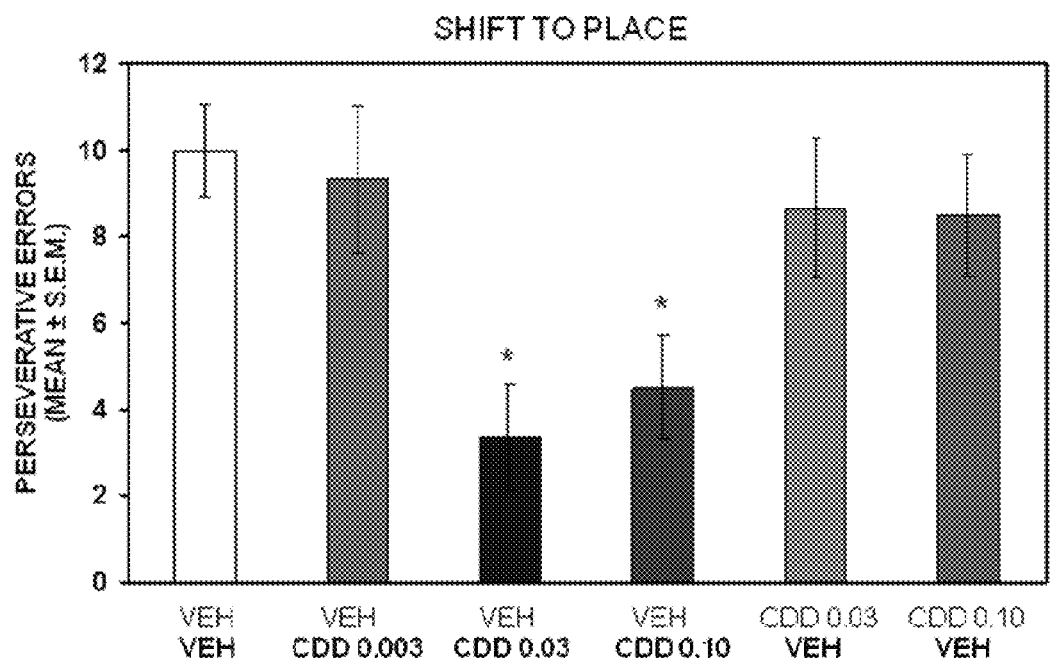
FIGS. 5A-C present graphs depicting the breakdown of the types of errors exhibited during the shift from a visual cue task to a place cue task. CDD-0102A, at doses of 0.03 and 0.1 mg/kg decreased the number of FIG. 5A) perseverative errors, and FIG. 5B) regressive errors with no significant impact on FI.G C) never-reinforced errors.
Figure 5B:
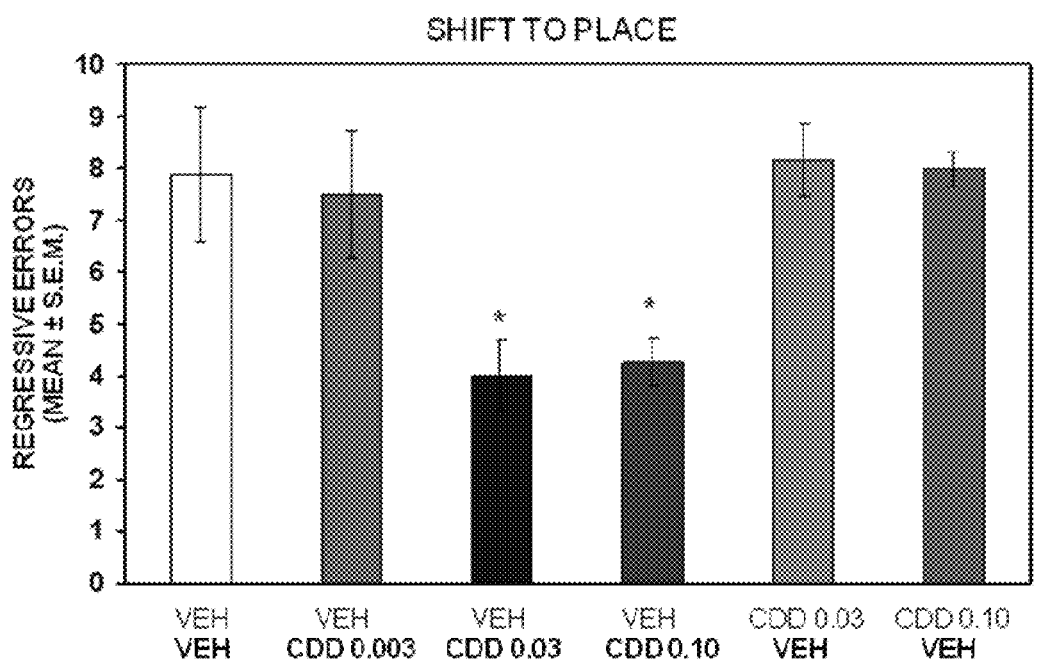
Figure 5C:
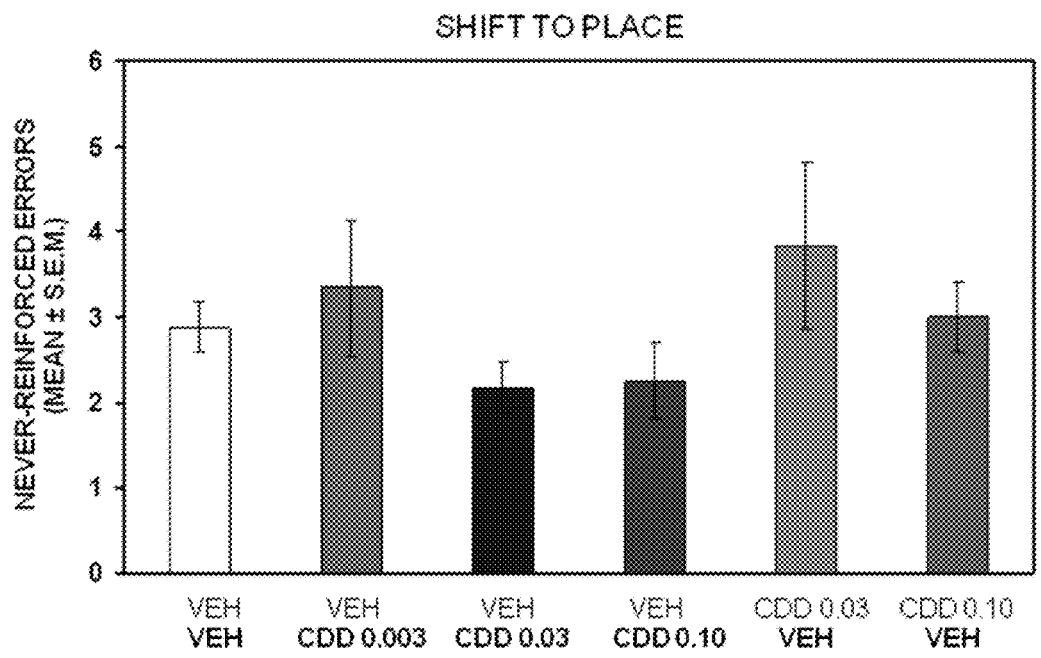

A similar analysis of the types of errors exhibited during the shift from a visual cue task to a place cue task is shown in FIGS. 5A-C. CDD-0102A, at doses of 0.03 and 0.1 mg/kg decreased the number of (FIG. 5A) perseverative errors (FIG. 5A), and regressive errors (FIG. 5B) with no significant impact on never-reinforced errors (FIG. 5C).

Figure 6:
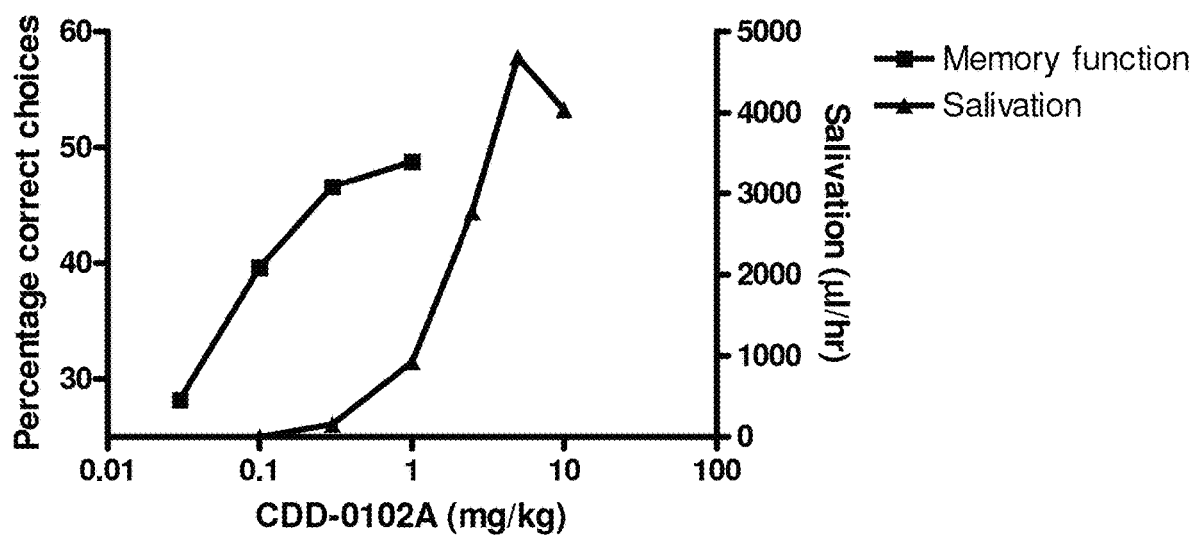
FIG. 6 presents a graph comparing the effects of CDD-0102A on memory function and salivation following i.p. injections in the rat.

A comparison of the effects on memory function (adapted from FIG. 2) with effects on salivation is shown in FIG. 6. Significant effects on memory function as measured by spontaneous alternation were observed with CDD-0102A at 0.1, 0.3 and 1.0 mg/kg i.p., while salivation was not observed until 0.3 mg/kg. Moreover, CDD-0102A was effective in enhancing learning of a place-visual cue task at a dose of 0.03 mg/kg i.p., a dose ten-fold lower than the lowest dose producing salivation. These comparisons suggest a good separation between efficacious doses and those producing adverse effects in rats.

The observed functional selectivity of CDD-0102A is unique among compounds purported to be selective $M_1$ agonists. Recent studies have indicated that a variety of compounds claimed to exhibit selective $M_1$ agonist activity activate multiple muscarinic receptors (Heinrich et al., 2008). The lack of selectivity likely contributes to the high incidence of adverse effects observed when the compounds are administered to humans. To assess selectivity for muscarinic receptors, the ability of CDD-0102A to activate responses was compared with the nonselective, full agonist carbachol at each muscarinic receptor subtype. In cultured cell lines expressing individual muscarinic receptor subtypes, phosphoinositide (PI) metabolism studies assessed activity at $M_1$, $M_3$ and $M_5$ receptors, while measures of cAMP levels examined $M_2$ and $M_4$ receptor activity.

As shown in Table 1 in FIG. 7, at $M_1$ receptors expressed in A9 L cells, CDD-0102 stimulated PI metabolism to 46% of the carbachol response with an $EC_{50}$ of 13 µM. At $M_3$ receptors expressed in A9 L cells, CDD-0102 stimulated PI metabolism to 6.6% of the carbachol response with an $EC_{50}$ of 10 µM. CDD-0102 was not active when $M_5$ receptors were expressed at low levels in A9 L cells. At higher levels of $M_5$ receptor expression, CDD-0102 stimulated PI metabolism to 28% of the carbachol response with an $EC_{50}$ of 7.5 µM. In addition, CDD-0102 was inactive in assays assessing the inhibition of adenylyl cyclase activity in A9 L cells expressing $M_2$ receptors and in CHO cells expressing $M_4$ receptors. Thus, CDD-0102 is a functionally-selective $M_1$ agonist with weaker activity at $M_5$ receptors, very weak activity at $M_3$ receptor and no activity at $M_2$ or $M_4$ receptors.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

These tests show that selective $M_1$ muscarinic cholinergic agonists, such as CDD-102A significantly enhanced delayed spontaneous alternation performance at the 0.1, 0.3 and 1.0 mg/kg doses. Thus, the CDD102A compounds are effective in enhancing cognitive function at dosages much lower than previously thought possible or achieved by other types of muscarinic agonists.

Experimental Procedures:

All testing was carried out in a four-arm cross-maze made of 0.6 cm thick black plastic was used for all behavioral testing. The maze was placed on a table that was 72 cm above the floor. Each arm was 55 cm long 10 cm wide. The height of the arm walls was 15.0 cm. Each arm contained a food well (3.2 cm diameter×1.6 cm high) that was 3 cm away from the end wall. Each food-well hole was 2.3 cm in diameter and 1.6 cm deep.

In the spontaneous alternation test, rats were placed in the testing room 5 min before testing. Rats were allowed to freely explore the maze for 15 min. after making a choice, a rat was blocked into that arm for 30 s. The block was a 21.5 cm×12 cm piece of plastic. After the 30-s delay, the block was removed and a rat was allowed to enter another arm. The number and sequence of arm entries was recorded. An arm entry was recorded when all four paws entered an arm. An alternation was defined as entry into four different arms on overlapping quadruple sets of arm entries; e.g., a quadruple set consisting of arm choices A, D, C, B was an alternation but a quadruple set consisting of arm choices A, D, A, C was not. The percent alternation score is equal to the ratio of (actual alternations/possible alternations) multiplied by 100; chance performance on this task is 22.2%. Rats that made less than 11 arm entries in 15 min were excluded from the analysis.

Thirty minutes prior to testing, each rat received a single intraperitoneal injection of one of the following treatments: 1) saline; 2) CDD-102A 0.03 mg/kg; 3) CDD-102A 0.1 mg/kg; 4) CDD-102A 0.3 mg/kg; 5) CDD-102A 1 mg/kg. The drug was mixed in saline Examples of Uses Thus, the present invention provides pharmaceutical compositions comprising a CDD-102A compound of the Formula I and a pharmaceutically acceptable diluent.

Routes of Administration

The compounds of Formula I can be administered by a variety of routes. In effecting treatment of a subject afflicted with disorders described herein, a CDD-102A compound of Formula I can be administered in any form or mode that makes the compound bioavailable in an effective amount, including oral and parenteral routes. For example, CDD-102A compounds of Formula I can be administered orally, by inhalation, or by the subcutaneous, intramuscular, intravenous, transdermal, intranasal, rectal, occular, topical, sublingual, buccal, or other routes. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the subject in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.001% of a compound of the invention, but may be varied to be between 0.001 and about 90% of the weight thereof. The amount of the CDD-102A compound of Formula I present in such compositions is such that a suitable dosage will be obtained. The solutions or suspensions may also include one or more of the following adjuvants: sterile diluents, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diaminetetraacetic acid; buffers, such as acetates, citrates or phosphates; and agents for the adjustment of tonicity, such as sodium chloride or dextrose. The parenteral preparation can be enclosed in ampules, disposable syringes or multiple dose vials made of glass or plastic. Preferred compositions and preparations are able to be determined by one skilled in the art.

The compounds of the present invention may also be administered topically, and when done so, the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of a CDD-102A compound of Formula I or its pharmaceutical salt from about 0.1 to about 10% w/v (weight per unit volume).

Utilities

As presented herein, the CDD-102A compound of Formula I is useful in the treatment of memory function symptoms, particularly a memory function, a learning function, and behavioral flexibility function; and more particularly, where the behavioral flexibility function includes one or more of: perseveration errors, regressive errors and never-reinforced errors.

Typically, the CDD-102A compounds are employed in a subject who has suffered at least one symptom event. Thus, the CDD-102A compounds invention are most typically employed to reduce the likelihood that the subject will further incur such symptoms.

Doses

The disorders associated with $M_1$ muscarinic receptors are treated by administering an effective amount of a CDD-102A compound or pharmaceutical composition of Formula I. An effective amount can be readily determined by the attending diagnostician, as one skilled in the art, by the use of conventional techniques and by observing results obtained under analogous circumstances. In determining an effective amount, the dose of a CDD-102A compound of Formula I, a number of factors are considered by the attending diagnostician, including, but not limited to: the CDD-102A compound of Formula I to be administered; the species of mammal—its size, age, and general health; the specific disorder involved; the degree of involvement or the severity of the disorder; the response of the individual subject; the mode of administration; the bioavailability characteristics of the preparation administered; the dose regimen selected; the use of other concomitant medication; and other relevant circumstances.

The specific dose administered is determined by the particular circumstances surrounding each situation. These circumstances can include: the route of administration, the prior medical history of the recipient, the symptom being treated, the severity of the symptom being treated, and the age of the recipient. The recipient subject's attending physician should determine the therapeutic dose administered in light of the relevant circumstances.

Also, it is to be understood that the exact dose may be determined, in accordance with the standard practice in the medical arts of "dose titrating" the recipient; that is, initially administering a low dose of the compound, and gradually increasing the dose until the desired therapeutic effect is observed.

It is to be further understood that the dosage regimen can be selected in accordance with a variety of factors. These include type, species, age, weight, sex and medical condition of the subject; the severity of the condition to be treated; the route of administration; the kidney and liver functions of the subject; and the particular compounds employed. A physician of ordinary skill can readily determine and prescribe the effective amount of the drug required to prevent, counter or arrest the progress of the disease or disorder that is being treated.

It is to be understood that the CDD102A compounds are effective in enhancing cognitive function at dosages much lower than previously thought possible or achieved by other types of muscarinic agonists.

In certain non-limiting examples, the daily dosage of the products may be varied over a wide range from about 0.0001 to about 10 mg per adult human per day. An effective amount of the drug can be supplied at a dosage level of about 0.001 mg/kg to about 10 mg/kg body weight per day. In certain embodiments, the range can be from about 0.1 to about 10 mg/kg of body weight per day; and in certain embodiments, from about 0.01 mg/kg to about 0.1 mg/kg of body weight per day. Also, in certain embodiments, the compounds may be administered on a regimen of 1 to 4 times per day.

It is also within the contemplated scope of the present invention that the CDD-102A analog compounds may be used alone at appropriate dosages defined by routine testing in order to obtain optimal pharmacological effect, while minimizing any potential toxic or otherwise unwanted effects. In addition, the CDD-102A compounds may be used as adjunctive therapy with known drugs to reduce the dosage required of these traditional drugs, and thereby reduce their side effects.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated.

The term "pharmaceutically acceptable addition salts" refers to salts known in the art to be acceptable in pharmaceutical practice, for example acid addition salts such as hydrochloric acid salts, maleic acid salts, and citric acid salts. Pharmaceutically acceptable acid addition salts include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like.

The term "metabolite" refers to a form of a compound obtained in a human or animal body by action of the body on the administered form of the compound, for example a de-methylated analogue of a compound bearing a methyl group which is obtained in the body after administration of the methylated compound as a result of action by the body on the methylated compound. Metabolites may themselves have biological activity.

The term "prodrug" refers to a form a compound which after administration to a human or animal body is converted chemically or biochemically to a different compound in the body having biological activity. A prodrug form of a compound may itself have biological activity.

Therefore, it is intended that the invention not be limited to the particular embodiment disclosed herein contemplated for carrying out this invention, but that the invention will include all embodiments falling within the scope of the claims.

REFERENCES

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

Carlsson, A.; Waters, N.; Holm-Waters, S.; Tedroff, J.; Nilsson, M. et al. Interactions between monoamines, glutamate, and GABA in schizophrenia: new evidence. *Annu Rev Pharmacol Toxicol* 2001, 41, 237-260.

Carlsson, A. The current status of the dopamine hypothesis of schizophrenia. *Neuropsychopharmacology* 1988, 1, 179-186.

Friedman, J. I.; Temporini, H.; Davis, K. L. Pharmacologic strategies for augmenting cognitive performance in schizophrenia. *Biol Psychiatry* 1999, 45, 1-16.

Hyman, S. E.; Fenton, W. S. Medicine. What are the right targets for psychopharmacology? *Science* 2003, 299, 350-351.

Abood, L. G.; Biel, J. H. Anticholinergic psychotomimetic agents. *Int Rev Neurobiol* 1962, 4, 217-273.

Cummings, J. L.; Back, C. The cholinergic hypothesis of neuropsychiatric symptoms in Alzheimer's disease. *Am J Geriatr Psychiatry* 1998, 6, S64-78.

Levy, M. L.; Cummings, J. L.; Kahn-Rose, R. Neuropsychiatric symptoms and cholinergic therapy for Alzheimer's disease. *Gerontology* 1999, 45 Suppl 1, 15-22.

Cummings, J. L. The role of cholinergic agents in the management of behavioural disturbances in Alzheimer's disease. *Int J Neuropsychopharmacol* 2000, 3, 21-29.

Bodick, N. C.; Offen, W. W.; Shannon, H. E.; Satterwhite, J.; Lucas, R. et al. The selective muscarinic agonist xanomeline improves both the cognitive deficits and behavioral symptoms of Alzheimer disease. *Alzheimer Dis Assoc Disord* 1997, 11, S16-22.

Bodick, N. C.; Offen, W. W.; Levey, A. I.; Cutler, N. R.; Gauthier, S. G. et al. Effects of xanomeline, a selective muscarinic receptor agonist, on cognitive function and behavioral symptoms in Alzheimer disease. *Arch Neurol* 1997, 54, 465-473.

Rasmussen, T.; Fink-Jensen, A.; Sauerberg, P.; Swedberg, M. D.; Thomsen, C. et al. The muscarinic receptor agonist BuTAC, a novel potential antipsychotic, does not impair learning and memory in mouse passive avoidance. *Schizophr Res* 2001, 49, 193-201.

Jones, C. K.; Shannon, H. E. Effects of scopolamine in comparison with apomorphine and phencyclidine on prepulse inhibition in rats. *Eur J Pharmacol* 2000, 391, 105-112.

Jones, C. K.; Shannon, H. E. Muscarinic cholinergic modulation of prepulse inhibition of the acoustic startle reflex. *J Pharmacol Exp Ther* 2000, 294, 1017-1023.

Felder, C. C.; Porter, A. C.; Skillman, T. L.; Zhang, L.; Bymaster, F. P. et al. Elucidating the role of muscarinic receptors in psychosis. *Life Sci* 2001, 68, 2605-2613.

Anagnostaras, S. G.; Murphy, G. G.; Hamilton, S. E.; Mitchell, S. L.; Rahnama, N. P. et al. Selective cognitive dysfunction in acetylcholine M1 muscarinic receptor mutant mice. *Nat Neurosci* 2003, 6, 51-58.

Seeger, T.; Fedorova, I.; Zheng, F.; Miyakawa, T.; Koustova, E. et al. M2 muscarinic acetylcholine receptor knock-out mice show deficits in behavioral flexibility, working memory, and hippocampal plasticity. *J Neurosci* 2004, 24, 10117-10127.

Harries, M H.; Samson, N A.; Cilia, J.; Hunter, A J. "The profile of sabcomeline (SB-202026), a functionally selective M1 receptor partial agonist, in the marmoset." British Journal of Pharmacology, v. 124 issue 2, 1998, p. 409-15.

Heinrich J N, Butera J A, Carrick T, Kramer A, Kowal D, Lock T, Marquis K L, Pausch M H, Popiolek M, Sun S C, Tseng E, Uveges A J, Mayer S C Pharmacological comparison of muscarinic ligands: historical versus more recent muscarinic M1-preferring receptor agonists. Eur J Pharmacol. v. 605 issue 1-3, 2009, p. 53-6.

What is claimed is:

1. A method of decreasing regressive errors while enhancing behavioral flexibility in a human subject in need thereof, comprising:
    administering to a subject in need thereof an effective amount of CDD-0102 [5-(3-ethyl-1,2,4-oxadiazol-5-yl)-1,4,5,6-tetrahydropyrimidine] compound or a pharmaceutically acceptable salt or hydrate thereof to selectively activate $M_1$ muscarinic receptors in the subject without substantially producing $M_2$, $M_3$, $M_4$ and/or $M_5$ muscarinic receptor subtype activity in the subject;
    wherein the compound is administered in a daily dosage ranging from about 0.01 mg/kg to about 0.3 mg/kg of body weight;

wherein the subject has autism spectrum disorders (ASD), does not have attention deficit hyperactivity disorder (ADHD) and does not have a cholinergic deficit, but does exhibit regressive errors;

wherein the subject is treated for regressive errors not associated with cholinergic deficits, but where cognitive function or behavioral flexibility is impaired;

wherein the regressive errors have already developed and the subject is protected against worsening of the regressive errors;

and, decreasing regressive errors by enhancing behavioral flexibility and increasing the ability to initially inhibit a previously relevant strategy and to maintain a new, relevant strategy once selected.

2. The method according to claim 1, wherein the compound is administered in a dosage unit as a solid formulation; in a dosage unit as a tablet or capsule formulation.

3. The method according to claim 1, wherein the compound is administered orally or by injection.

4. The method according to claim 1, wherein the subject is evaluated before, during and/or after administration of the compound to determine efficacy of the treatment.

5. The method according to claim 1, including obtaining systemic measurements of the levels of the compound at various time points after administration of the compound.

* * * * *